(12) United States Patent
Verkman et al.

(10) Patent No.: US 10,702,506 B2
(45) Date of Patent: Jul. 7, 2020

(54) SMALL MOLECULE INHIBITORS OF PENDRIN ION EXCHANGE AND PHARMACEUTICAL COMPOSITIONS

(71) Applicant: THE REGENTS OF THE UNIVERSITY OF CALIFORNIA, Oakland, CA (US)

(72) Inventors: Alan S. Verkman, Oakland, CA (US); Peter M. Haggie, Oakland, CA (US); Onur Cil, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/079,019

(22) PCT Filed: Feb. 24, 2017

(86) PCT No.: PCT/US2017/019506
§ 371 (c)(1),
(2) Date: Aug. 22, 2018

(87) PCT Pub. No.: WO2017/147523
PCT Pub. Date: Aug. 31, 2017

(65) Prior Publication Data
US 2019/0054071 A1    Feb. 21, 2019

Related U.S. Application Data

(60) Provisional application No. 62/300,411, filed on Feb. 26, 2016.

(51) Int. Cl.
*A61K 31/44*    (2006.01)
*A61K 31/437*   (2006.01)
(Continued)

(52) U.S. Cl.
CPC ........ *A61K 31/437* (2013.01); *A61K 31/4155* (2013.01); *A61K 31/635* (2013.01);
(Continued)

(58) Field of Classification Search
CPC .............. A61K 31/437; A61K 31/4155; A61K 2300/00; A61P 31/12; A61P 31/04; A61P 11/00
(Continued)

(56) References Cited

U.S. PATENT DOCUMENTS

2009/0156611 A1   6/2009   Oinas et al.
2010/0331295 A1   12/2010  Busch et al.

FOREIGN PATENT DOCUMENTS

EP    2 370 437 B1    11/2009
EP    2 716 632 A1    4/2014
(Continued)

OTHER PUBLICATIONS

International Search Report and Written Opinion, dated Apr. 14, 2017, for International Application No. PCT/US17/19506, 14 pages.
(Continued)

*Primary Examiner* — Taylor V Oh
(74) *Attorney, Agent, or Firm* — Seed IP Law Group LLP

(57) ABSTRACT

Provided herein are small molecule inhibitors of pendrin. More specifically, the small molecules disclosed herein may be used to inhibit pendrin-mediated anion exchange. These small molecules may be used for treatment of diseases and disorders that are treatable by inhibiting pendrin, such as cystic fibrosis, rhinitis, chronic rhinosinusitis, exposure to an industrial toxin, certain viral infections, certain bacterial infections, and chronic obstructive pulmonary disease. The small molecules may further be used to potentiate a diuretic effect of a diuretic compound. The small molecules may additionally be used to treat hypertension or thyroid conditions.

19 Claims, 24 Drawing Sheets

(51) Int. Cl.
*A61K 31/4155* (2006.01)
*C07D 471/04* (2006.01)
*A61K 45/06* (2006.01)
*A61K 31/635* (2006.01)
*C07D 409/04* (2006.01)
*A61P 31/12* (2006.01)
*A61P 31/04* (2006.01)
*A61P 11/00* (2006.01)

(52) U.S. Cl.
CPC ............ *A61K 45/06* (2013.01); *A61P 11/00* (2018.01); *A61P 31/04* (2018.01); *A61P 31/12* (2018.01); *C07D 409/04* (2013.01); *C07D 471/04* (2013.01); *A61K 2300/00* (2013.01)

(58) Field of Classification Search
USPC ........................................................ 514/303
See application file for complete search history.

(56) References Cited

FOREIGN PATENT DOCUMENTS

WO 2010/126002 A1 11/2010
WO 2014/141035 A2 9/2014

OTHER PUBLICATIONS

National Center for Biotechnology Information, "N-phenyl-5-(1 H-pyrazol-5-yl)thiophene-2-sulfonamide; STOCK6S-89573; MolPort-008-341-102; STK939229; ZINC36358167; AKOS005668168,"
Pubchem CID 45492877, downloaded on Apr. 4, 2017 from https://pubchem.ncbi.nlm.nih.gov/compound/45492877#section=, 9 pages.
National Center for Biotechnology Information, "MolPort-010-662-536; HMS3558918; ZINC33306757; AKOS005053584; MCULE-2077867536," PubChem CID 50842869, downloaded on Apr. 4, 2017 from https://pubchem.ncbi.nlm.nih.gov/compound/50842869#section=, 10 pages.
National Center for Biotechnology Information, "MolPort-010-708-724; ZINC64565872; AKOS021862839; MCULE-6139235915; N-(3,4-dimethylphenyl)-1-methyl-3-{[(4-methylbenzyl)oxy]methyl}-1,4,6,7-tetrahydro-5H-pyrazolo[4,3-c]pyridine-5-carboxamide," PubChem CID 53018317, downloaded on Apr. 5, 2017 from https://pubchem.ncbi.nlm.nih.gov/com pound/53018317#section=, 10 pages.
National Center for Biotechnology Information, "MolPort-010-708-793; ZINC64565942; AKOS021863222; MCULE-5230925452; N-(4-ethylphenyl)-1-methyl-3-(phenoxymethyl)-1,4,6,7-tetrahydro-5H-pyrazolo[4,3-c]pyridine-5-carboxamide," PubChem CID 53018386, downloaded on Apr. 5, 2017 from https://pubchem.ncbi.nlm.nih.gov/compound/53018386#section=, 9 pages.
National Center for Biotechnology Information, "MolPort-010 708-795; ZINC64565944; AKOS021863134; MCULE-4115267859; N-(3,4 dimethylphenyl)-1-methyl-3-(phenoxymethyl)-1,4,6,7-tetrahydro-5H-pyrazolo[4,3-c]pyridine-5-carboxamide," PubChem CID 53018388, downloaded on Apr. 5, 2017 from https://pubchem.ncbi.nlm.nih.govlcompound/53018388#section=, 9 pages.
Jia et al., "Pendrin, an anion exchanger on lung epithelial cells, could be a novel target for lipopolysaccharide-induced acute lung injury mice," *Am J Transl Res* 8(2):981-992, 2016.
Manley et al., "The BeWo Choriocarcinoma Cell Line as a Model of Iodide Transport by Placenta," *Placenta* 26:380-386, 2005.
Soleimani, "The multiple roles of pendrin in the kidney," *Nephrol Dial Transplant* 30:1257-1266, 2015.
Supplementary European Search Report, dated Oct. 9, 2019, for European Application No. 17757376.3, 11 pages.

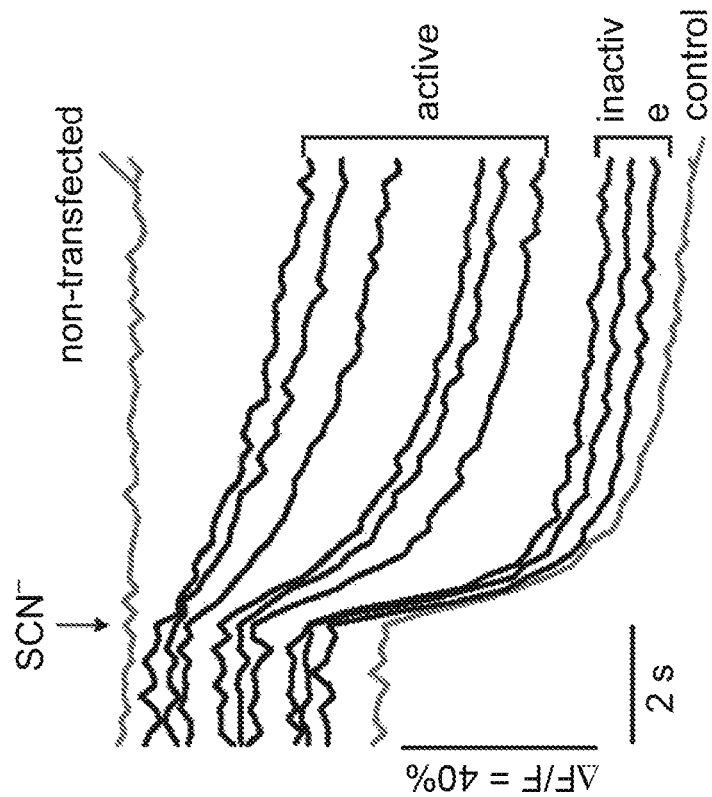
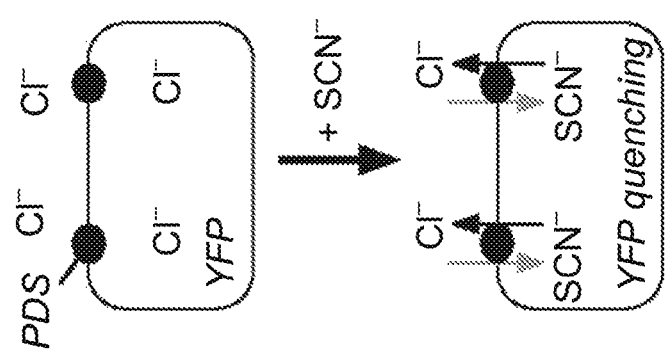
FIG. 1B
FIG. 1A

Class A

Best R¹ = 4-OMe, 4-Et, 4-Cl, 4-Me, 4-SMe, 3F, 4-OMe

Moderate R¹ = 3-SMe, 3-Et, 3-Cl

Class C inactive: 4-pyrazole
active: 2- or 3-sulfonamide

PDS$_{inh}$-C01 inactive: 4-pyrazole active: 2- or 3-sulfonamide active: 3',4'-CH$_3$, moderate: 3'-CH$_3$, 3'CF$_3$ R = active     moderate     inactive

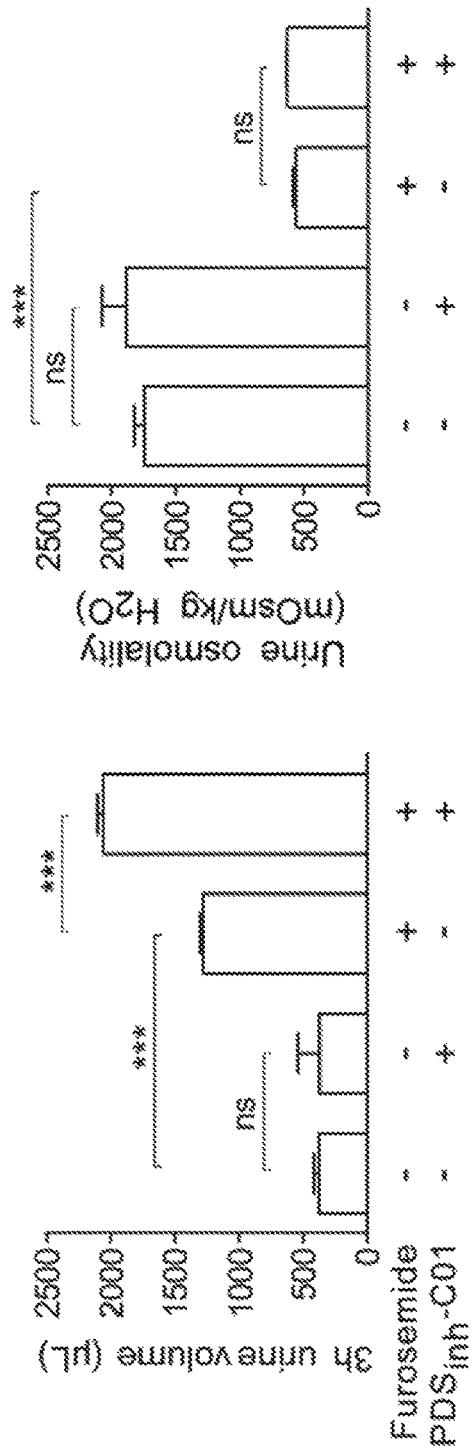
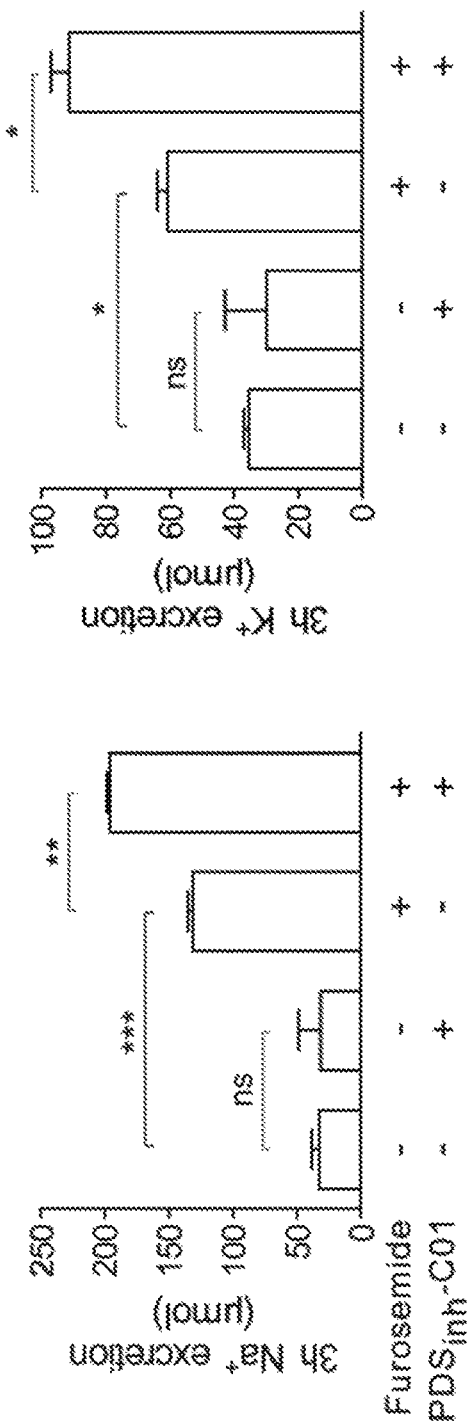
FIG. 11B
FIG. 11C

SMALL MOLECULE INHIBITORS OF PENDRIN ION EXCHANGE AND PHARMACEUTICAL COMPOSITIONS

STATEMENT OF GOVERNMENT INTEREST

This invention was made with government support under Grant Nos. P30 DK072517, DK101373, DK035124, DK099803, R37 EB000415, EY013574, AI111634, and P30 CA082103 awarded by the National Institutes of Health. The government has certain rights in this invention.

BACKGROUND

Technical Field

This disclosure relates to pharmaceutical composition of small molecule pendrin inhibitors and methods for treating diseases and disorders related to aberrant ion exchange activity, such as cystic fibrosis, salt-sensitive hypertension, edema, cirrhosis, and certain renal disorders.

Description of the Related Art

Aberrant anion exchange is implicated in a variety of human diseases and disorders. For example, solute imbalances in plasma or urine may indicate renal, cardiac, or hepatic issues. In cystic fibrosis (CF), defective Cl⁻ and $HCO_3^-$ transport alters the volume and composition of airway surface liquid (ASL), which may lead to a variety of complications such as impaired immune function and CD disease pathogenesis. Thus, cellular mechanisms involved in anion exchange are of interest as potential therapeutic targets.

Pendrin, encoded by the SLC26A4 (solute carrier family 26, member 4) gene, is an anion exchanger expressed in a variety of tissues, including the epithelium of inflamed airways, the inner ear, the thyroid, the adrenal gland, and the kidneys.

Pendrin is implicated in airways diseases. Pendrin expression is upregulated in a variety of airway disease contexts, such as, for example: airway epithelial cultures that are chronically exposed to cytokines such as IL-13, IL-4, and IL-17A; rodent models of inflammatory lung disease, including allergen (ovalbumin, OVA)-induced asthma, chronic obstructive pulmonary disease (COPD), infection, and industrial toxin exposure; and, humans with rhinovirus infection, asthma, CF, rhinitis, and chronic rhinosinusitis. The best previously described pendrin inhibitor, niflumic acid, produces <40% inhibition at 100 µM and has poor specificity. Drug candidates capable of effecting anion exchangers such as pendrin are needed.

BRIEF SUMMARY

Provided herein are pharmaceutical compositions comprising compounds that are potent inhibitors of pendrin activities. Also disclosed are methods for treating diseases, disorders, and conditions that are treatable by inhibiting pendrin-mediated anion exchange by administrating the pharmaceutical composition provided herein. The pharmaceutical compositions of the present disclosure may also be used in conjunction with a diuretic, such as a loop diuretic, to potentiate diuresis. The following embodiments are provided herein.

Some embodiments provide for pharmaceutical compositions comprising a pharmaceutically acceptable excipient and a compound of Formula (I):

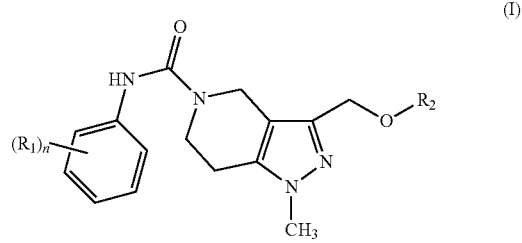

(I)

wherein n is 0, 1, 2, or 3; $R^1$ at each occurrence is the same or different and independently optionally substituted alkyl, optionally substituted alkoxy, halo, trifluoroalkyl, or optionally substituted thioalkyl; and $R^2$ is optionally substituted aryl or optionally substituted aralkyl.

In a more specific embodiment, the compound is represented by Formula (Ia):

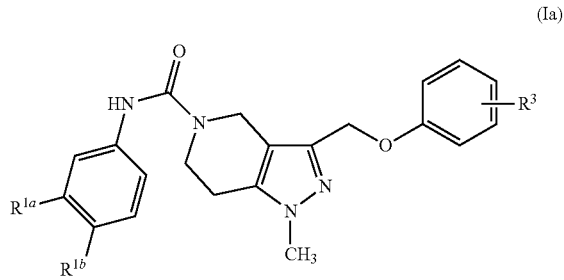

(Ia)

wherein,
$R^{1a}$ and $R^{1b}$ are the same or different and independently hydrogen, optionally substituted alkyl, optionally substituted alkoxy, halo, trifluoroalkyl, or optionally substituted thioalkyl;
$R^3$ is hydrogen or halo.

In another more specific embodiment, the compound is represented by Formula (Ib):

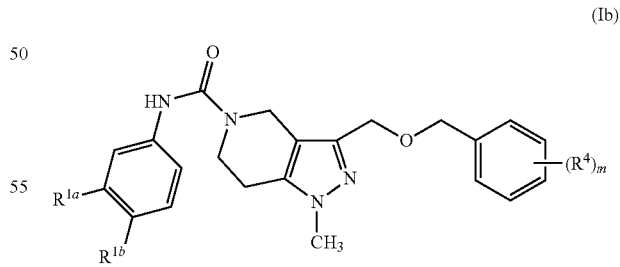

(Ib)

wherein,
m is 0, 1 or 2;
$R^{1a}$ and $R^{1b}$ are the same or different and independently hydrogen, optionally substituted alkyl, optionally substituted alkoxy, halo, trifluoroalkyl, or optionally substituted thioalkyl; and
each $R^4$ is the same or different and independently optionally substituted alkyl or halo.

Other embodiments provide for pharmaceutical compositions comprising a pharmaceutically acceptable excipient and a pyrazolothiophenesulfonamide compound represented by Formula (II):

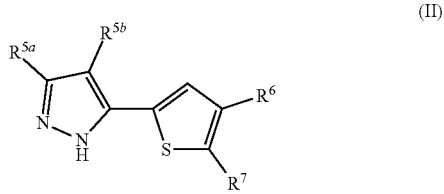

(II)

wherein $R^{5a}$ and $R^{5b}$ are the same or different and independently hydrogen, or optionally substituted alkyl; $R^6$ and $R^7$ are the same or different and independently hydrogen, optionally substituted alkyl, or —S(O)$_2$NHR, provided one of $R^6$ and $R^7$ is —S(O)$_2$NHR; and R is optionally substituted aryl or optionally substituted cycloalkyl.

Other embodiments provide for methods of treating an airway disease in a subject in need thereof comprising administering to the subject a therapeutically effective amount of one or more of the pharmaceutical compositions described above.

Still other embodiments provide for methods of treating cystic fibrosis in a subject in need thereof comprising administering to the subject a therapeutically effective amount of one or more of the pharmaceutical compositions described above.

Other embodiments provide for methods of treating a disease or condition treatable by inhibiting pendrin, partially or completely, in a subject in need thereof comprising administering to the subject a therapeutically effective amount of one or more of the pharmaceutical compositions described above.

Further embodiments provide for methods for promoting diuresis to a subject in need thereof comprising: administering to the subject a diuretic; and administering to the subject a therapeutically effective amount of one or more of the pharmaceutical compositions described above, wherein the one or more pharmaceutical composition is administered prior to, contemporaneous with, or following administration of the diuretic to the subject.

Other embodiments provide methods for treating hypertension or edema in a subject in need thereof comprising: administering to the subject a diuretic; and administering to the subject a therapeutically effective amount of one or more of the pharmaceutical compositions described above, wherein the one or more pharmaceutical composition is administered prior to, contemporaneous with, or following administration of the diuretic to the subject.

Further embodiments provide for use of one or more of the pharmaceutical compositions described above for airway disease therapy. Other embodiments provide for use of one or more of the pharmaceutical compositions described above for combination therapy with a diuretic.

Other embodiments provide for methods of method of treating hypertension comprising administering to a subject in need thereof a therapeutically effective amount of the one or more of the pharmaceutical compositions described above.

Still other embodiments provide for methods of treating a thyroid condition comprising administering to a subject in need thereof a therapeutically effective amount one or more of the pharmaceutical compositions described above.

BRIEF DESCRIPTION OF THE DRAWINGS

FIGS. 1A-1D illustrate pendrin-inhibiting compounds identified by high-throughput screening and summarize experimental approaches used to characterize the inhibitory activity. FIG. 1A shows a schematic of assay showing extracellular addition of SCN⁻ results in pendrin-mediated Cl⁻/SCN⁻ exchange and YFP quenching. FIG. 1B shows representative time course of YFP fluorescence quenching in cells expressing YFP alone (non-transfected, top) and YFP with human pendrin, showing curves for active and inactive compounds (and no test compound "control"). FIG. 1C shows the chemical structures of pendrin inhibitors identified from the screen. FIG. 1D shows the structural determinants of activity of compounds of Formula (I) (left) and compounds of Formula (II) (right).

FIG. 2A shows original fluorescence quenching curves for inhibition of pendrin-mediated Cl⁻/SCN⁻ (left) and Cl⁻/I⁻ (right) exchange by PDS$_{inh}$-A01 (top) and PDS$_{inh}$-C01 (bottom). Data shown in FIG. 2B illustrates concentration-dependent inhibition of pendrin-mediated Cl⁻/SCN⁻, and Cl⁻/I⁻ and Cl⁻/NO$_3$⁻ exchange by PDS$_{inh}$-A01 (top) and PDS$_{inh}$-C01 (bottom). IC$_{50}$ values for Cl⁻/SCN⁻ exchange for both compounds were ~9 μM. PDS$_{inh}$-A01 and PDS$_{inh}$-C01 inhibited Cl⁻/I⁻ and Cl⁻/NO$_3$⁻ exchange with IC$_{50}$ of ~8 μM and –5 μM, respectively. FIG. 2C shows inhibition kinetics of pendrin-mediated Cl⁻/SCN⁻ exchange in which 10 μM PDS$_{inh}$-A01 was added for indicated times (left) and summary (right) for PDS$_{inh}$-A01 and PDS$_{inh}$-C01. FIG. 2D shows data from washout experiments illustrating that inhibition of pendrin by PDS$_{inh}$-A01 and PDS$_{inh}$-C01 is reversible. All data shown as mean±SEM (n=4).

FIG. 3A depicts a schematic assay showing replacement of extracellular Cl⁻ for gluconate in BCECF-loaded FRT cells expressing human pendrin causes Cl⁻ efflux and HCO$_3$⁻ influx, resulting in cytoplasmic alkalinization. FIG. 3B presents representative BCECF fluorescence data showing inhibition of Cl⁻/HCO$_3$⁻ exchange by PDS$_{inh}$-A01 and PDS$_{inh}$-C01. FIG. 3C. Concentration-dependent inhibition of pendrin-mediated Cl⁻/HCO$_3$⁻ exchange by PDS$_{inh}$-A01 and PDS$_{inh}$-C01 (mean±SEM, n=3-9 cultures). FIG. 3D shows the control study done in non-transfected and pendrin expressing cells in the absence of HCO$_3$⁻. BCECF ratio imaging indicated an initial cytoplasmic pH of ~7.3 in all cultures studied.

FIG. 4A shows short-circuit current (I$_{sc}$) in IL-13-treated human bronchial epithelial (HBE) cells in response to agonists and inhibitors that target key ion transport processes: 20 μM amiloride; 20 μM forskolin; 10 μM CFTR$_{inh}$-172; 100 mM ATP. Experiments were done in the absence (left, top) and presence (left, bottom) of PDS$_{inh}$-A01 (25 μM, 30 minute pretreatment). (right) Summary of μI$_{sc}$ data (mean±SEM, n=3, differences not significant). FIG. 4B shows YFP quenching assay indicating effects of PDS$_{inh}$-A01 (25 μM, 30 min does not inhibit SCN⁻ transport by human SLC26A3 as assayed by YFP fluorescence responses after application of a 70 mM SCN⁻ gradient. Differences not significant on SCN⁻ transport by human SLC26A3 (the human protein most similar to pendrin in sequence; ~50% identity) after application of a 70 mM $SCN^-$ gradient. Fluorescence responses (left) and data summary (right) are shown (mean±SEM, n=17-cells, differences not significant).

FIG. 5A shows BCECF fluorescence in HBE and CFBE cells in response to extracellular $Cl^-$ replacement by gluconate in control (left) and IL-13 (right)-treated cells, with $PDS_{inh}$-A01 (25 μM, 30 min) as indicated. FIG. 5B presents a data summary (mean±SEM, n=3-4 cultures; * p<0.05 comparing without vs. with $PDS_{inh}$-A01). FIG. 5C. $PDS_{inh}$-A01 (25 μM, 4 hours) does not alter ASL pH, with data shown for HBE and CFBE cells under control and IL-13-treated conditions (mean±SEM, n=3-7 cultures; * p<0.005; ** p<0.05). BCECF ratio imaging indicated an initial cytoplasmic pH of ~7.3 in all cultures studied.

FIG. 6A shows reconstructions of confocal z-stacks showing rhodamine dextran-labeled ASL in HBE and CFBE cells, without and with IL-13-treatment. $PDS_{inh}$-A01 was used at 25 μM. FIG. 6B shows a summary of ASL depth (mean±SEM, n=6-12 cultures; * p<0.05 compared to HBE cultures (no IL-13); ** p<0.05 compared to IL-13-treated cultures; IL-13 increased ASL depth for all conditions compared to no IL-13-treatment.

FIG. 7A. $PDS_{inh}$-C01 is comprised of a thiophene with a sulfonamide group and a pyrazole heterocycle linked at the 3- and 5-positions, respectively. Structure-activity studies showed that changing the pyrazole from 5- to 4-position abolished activity and that a sulfonamide group at the 2- or 3-position was needed for inhibition activity. Limited substituents on the pyrazole were studied, with 3',4'-dimethyl giving the most potent compounds followed by 3'-methyl and trifluoromethyl. Substitution on the sulfonamide affected activity, with electron-neutral rings such as tetrahydro-naphthalene and 2-ethylphenyl giving best activity, whereas halide-substituted phenyl ring reduced activity. FIG. 7B. Functional studies of pendrin-mediated $Cl^-$ exchange for $I^-$, $SCN^-$ and $NO_3^-$ were done in FRT cells stably expressing murine pendrin and a YFP halide-sensing fluorescent indicator. (top) Schematic representation of fluorescence quenching assay for pendrin-mediated ion exchange in the presence of a pendrin inhibitor. (bottom) Fluorescence quenching data indicating ion exchange activity at various $PDS_{inh}$-C01 concentrations. FIG. 7C. Summary of pendrin inhibition by $PDS_{inh}$-C01. FIG. 7D. Pendrin-mediated $Cl^-/HCO_3^-$ exchange was measured by the kinetics of intracellular pH, using BCEC fluorescence as a cytoplasmic pH sensor, following extracellular addition of $HCO_3^-/CO_2$-containing buffer to drive $Cl^-$ efflux, $HCO_3^-$ influx, and consequent cytoplasmic alkalinization. FIG. 7E. Concentration-dependent effects of $PDS_{inh}$-C01 on the kinetics of $Cl^-/HCO_3^-$ exchange, the activity of pendrin with relevance to kidney function, were measured in a concentration-dependent manner with $IC_{50}$ ~1.2 μM. FIG. 7F. Selectivity data illustrating insignificant inhibition by $PDS_{inh}$-C01 of solute carrier proteins Slc4a1 (AE1), Slc26a3 (CLD/DRA) or NKCC1 (Slc12a2).

FIGS. 8A and 8C show original LC/MS data and linear standard curves in plasma and urine in which known amounts of $PDS_{inh}$-C01 were added to plasma and urine from untreated mice. FIGS. 8B and 8D summarize $PDS_{inh}$-C01 concentrations in plasma and urine following bolus interaperitoneal (ip) administration of 10 mg/kg $PDS_{inh}$-C01, showing predicted therapeutic concentrations for several hours.

FIG. 9A shows similar 3-h urine volume and osmolality in two different strains of mice treated with vehicle or $PDS_{inh}$-C01, even at a very high dose of 50 mg/kg. $PDS_{inh}$-C01 administration did not significantly change urine pH (FIG. 9B) or blood gas values (FIG. 9C), nor did it affect 3-h urinary salt excretion (FIG. 9D).

FIG. 10A. $PDS_{inh}$-C01 (10 mg/kg) significantly increased urine volume by ~30% at each dose of furosemide tested, without effect on urine osmolality. The diuretic effect was significantly greater than that produced by maximal furosemide (50 mg/kg). Increasing $PDS_{inh}$-C01 dose to 50 mg/kg did not further potentiate the furosemide effect. $PDS_{inh}$-C01, when given with 20 mg/kg furosemide, did not affect urine pH (FIG. 10B), but produced a compensated metabolic alkalosis (FIG. 10C). To rule out an inhibitory effect of furosemide on pendrin activity that could confound the physiological data, in vitro measurements showed no effect of furosemide on pendrin activity (FIG. 10E).

FIGS. 11A-11C further illustrate that pendrin inhibition potentiates the diuretic action of furosemide in a chronical treatment model. Because chronic loop diuretic treatment upregulates renal pendrin expression, which might potentiate the diuretic efficacy of pendrin inhibition, the action of $PDS_{inh}$-C01 in a chronic furosemide treatment model was studied. After 8 days of furosemide treatment, $PDS_{inh}$-C01 further potentiated the furosemide effect. FIG. 11B shows a ~60% increase in urine volume following $PDS_{inh}$-C01 in the chronically furosemide-treated mice, without effect on urine osmolality. FIG. 11C shows that $PDS_{inh}$-C01 significantly increased urinary $Na^+$ and $K^+$ excretion.

DETAILED DESCRIPTION

Figure 1C:
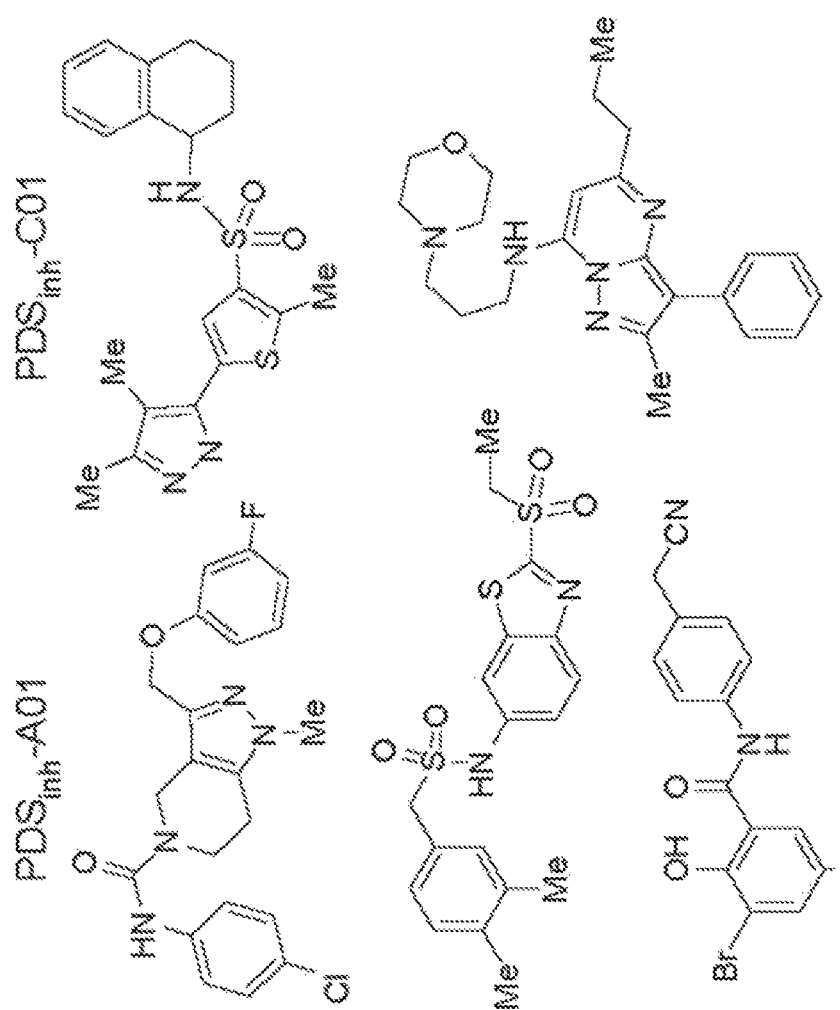

Small-molecule inhibitors of pendrin are described herein, as are pharmaceutical compositions comprising the same. Various embodiments are directed to methods for treating a variety of airway diseases or conditions, such as, for example, CF, rhinovirus infection, asthma, rhinitis, chronic rhinosinusitis, certain viral or bacterial infections, and exposure to industrial toxins. Other embodiments are directed to methods of potentiating diuresis in a subject in need thereof.

Pendrin Activities

Pendrin consists of 780 amino acids with a predicted cytoplasmic amino terminus and twelve membrane-spanning regions. Pendrin was identified by positional cloning in subjects with Pendred syndrome, an autosomal recessive disorder associated with congenital hearing loss and thyroid goiter.

Functional studies show that pendrin mediates electroneutral exchange of $Cl^-$ with various anions, including $I^-$, $HCO_3^-$, $OH^-$, $NO_3^-$, $SCN^-$ (thiocyanate) and $HCO_2^-$ (formate). In the inner ear, pendrin is expressed in the apical membrane of epithelial cells in the sensory (saccule, utricle, and ampullae) and non-sensory (endolymphatic sac) domains, and is implicated in determining inner ear luminal fluid volume and composition. In the thyroid, pendrin is expressed on the apical membrane of follicular cells, where it facilitates I⁻ efflux into the follicle colloid for thyroid hormone synthesis. In the kidney, pendrin is expressed in the apical plasma membrane of type B and non-A/non-B intercalated cells in the aldosterone-sensitive distal nephron, where it facilitates Cl⁻ absorption and $HCO_3^-$ secretion, in addition to being involved in Na⁺ absorption and acid-base balance.

Pendrin Inhibitors and Pharmaceutical Compositions

Various embodiments are directed to small molecules that selectively inhibit pendrin activities (e.g., pendrin-mediated anion exchange) at low micromolar potency. These compounds were identified by a functional, cell-based screen of a small molecule library and were found to produce strong and sustained impairment of pendrin-mediated ion exchange activity when pendrin showed elevated expression. Thus, pharmaceutical compositions comprising these pendrin inhibitors are suitable for treating diseases and disorders (including pulmonary and renal diseases) treatable by inhibiting pendrin.

One embodiment provides a pharmaceutical composition comprising a pharmaceutically acceptable excipient and a tetrahydropyrazolopyridine compounds represented by Formula (I):

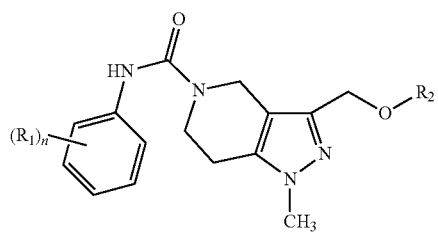

wherein, n is 0, 1, 2, or 3;

$R^1$ at each occurrence is the same or different and independently optionally substituted alkyl, optionally substituted alkoxy, halo, trifluoroalkyl, or optionally substituted thioalkyl; and $R^2$ is optionally substituted aryl or optionally substituted aralkyl.

In various embodiments, $R^1$ is $C_1$-$C_4$ alkyl, or $R^1$ is $C_1$-$C_4$ alkoxy, or $R^1$ is $C_1$-$C_4$ thioalkyl.

In other embodiments, $R^1$ is fluoro, trifluoroalkyl, or chloro.

In preferred embodiments, $R^1$ is not at the ortho-position of the phenyl ring.

In certain embodiments, $R^2$ is phenyl or substituted phenyl.

In a further embodiment, $R^2$ is phenyl substituted with one or more halo (e.g., fluoro). In preferred embodiments, $R^2$ is phenyl substituted with fluoro.

In yet another embodiment, $R^2$ is benzyl or substituted benzyl. In a preferred embodiment, $R^2$ is benzyl.

In a further embodiment, $R^2$ is benzyl in which the phenyl moiety is substituted with one or more alkyl (e.g., $C_1$-$C_4$ alkyl) or halo (e.g., fluoro). In preferred embodiments, $R_2$ is benzyl substituted with fluoro. In other embodiments, $R_2$ is benzyl substituted with methyl.

In a more specific embodiment, the tetrahydropyrazolopyridine compounds are represented by Formula (Ia):

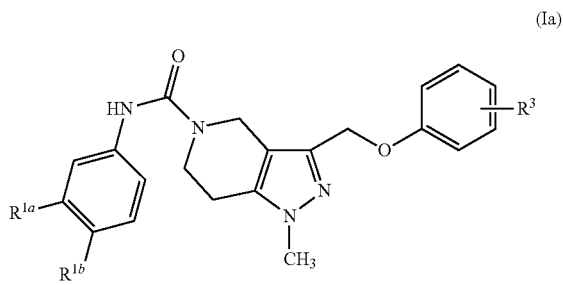

wherein, $R^{1a}$ and $R^{1b}$ are the same or different and independently hydrogen, optionally substituted alkyl, optionally substituted alkoxy, halo, trifluoroalkyl, or optionally substituted thioalkyl;

$R^3$ is hydrogen or halo.

In various embodiments, $R^{1a}$ and $R^{1b}$ are independently $C_1$-$C_4$ alkyl, $C_1$-$C_4$ alkoxy, $C_1$-$C_4$ thioalkyl, trifluoroalkyl, or halo. In more specific embodiments, $R^{1a}$ and $R^{1b}$ are the same or different and independently methyl, ethyl, methoxy, thiomethyl, trifluoromethyl, fluoro, or chloro.

In preferred embodiments, when $R^{1a}$ is hydrogen, $R^{1b}$ is $C_1$-$C_4$ alkyl, $C_1$-$C_4$ alkoxy, $C_1$-$C_4$ thioalkyl or halo. In more specific embodiments, when $R^{1a}$ is hydrogen, $R^{1b}$ is methyl, ethyl, methoxy, thiomethyl, or chloro.

In other embodiments, when Rib is hydrogen, $R^{1a}$ is $C_1$-$C_4$ alkyl, $C_1$-$C_4$ alkoxy, $C_1$-$C_4$ thioalkyl, trifluoroalkyl, or halo. In more specific embodiments, when $R^{1b}$ is hydrogen, $R^{1a}$ is methyl, ethyl, methoxy, trifluoromethyl, thiomethyl, fluoro, or chloro.

In preferred embodiments, $R^3$ is hydrogen. In other preferred embodiments, $R^3$ is fluoro, including 3-, or 4-substituted fluoro.

Table 1 provides specific compounds of Formula (Ia) and their respective percentage inhibition of human pendrin. These compounds demonstrated strong inhibition (at least 45% inhibition) at 25 µM. In comparison, the only known pendrin inhibitor, niflumic acid, showed less than 40% inhibition at 100 µM.

TABLE 1

| Compounds of Formula (Ia) | Inh. (%) |
|---|---|
| (structure shown) PDS$_{inh}$-A01 | 100 |

TABLE 1-continued

| Compounds of Formula (Ia) | Inh. (%) |
|---|---|
| [structure: 4-(methylthio)phenyl urea, 3-(phenoxymethyl)-1-methyl-tetrahydropyrazolo pyridine] | 77 |
| [structure: 4-chlorophenyl urea, 3-(phenoxymethyl)-1-methyl-tetrahydropyrazolo pyridine] | 72 |
| [structure: 3-fluoro-4-methoxyphenyl urea, 3-(phenoxymethyl)-1-methyl-tetrahydropyrazolo pyridine] | 69 |
| [structure: 4-chlorophenyl urea, 3-((4-fluorophenoxy)methyl)-1-methyl-tetrahydropyrazolo pyridine] | 66 |
| [structure: 3,4-dimethylphenyl urea, 3-(phenoxymethyl)-1-methyl-tetrahydropyrazolo pyridine] | 64 |
| [structure: 4-methylphenyl urea, 3-(phenoxymethyl)-1-methyl-tetrahydropyrazolo pyridine] | 61 |
| [structure: 3-chloro-4-methylphenyl urea, 3-((4-fluorophenoxy)methyl)-1-methyl-tetrahydropyrazolo pyridine] | 61 |
| [structure: 3,4-dimethylphenyl urea, 3-((4-fluorophenoxy)methyl)-1-methyl-tetrahydropyrazolo pyridine] | 58 |
| [structure: 3-chlorophenyl urea, 3-((3-fluorophenoxy)methyl)-1-methyl-tetrahydropyrazolo pyridine] | 60 |
| [structure: 3-trifluoromethylphenyl urea, 3-((4-fluorophenoxy)methyl)-1-methyl-tetrahydropyrazolo pyridine] | 57 |
| [structure: 4-ethylphenyl urea, 3-(phenoxymethyl)-1-methyl-tetrahydropyrazolo pyridine] | 54 |
| [structure: 3-chloro-4-fluorophenyl urea, 3-((4-fluorophenoxy)methyl)-1-methyl-tetrahydropyrazolo pyridine] | 54 |

TABLE 1-continued

| Compounds of Formula (Ia) | Inh. (%) |
|---|---|
| (structure with 3-fluoro-4-methoxyphenyl urea and 4-fluorophenoxymethyl) | 53 |
| (structure with 3-(methylthio)phenyl urea and phenoxymethyl) | 45 |

In another more specific embodiment, the tetrahydropyrazolopyridine compounds are represented by Formula (Ib):

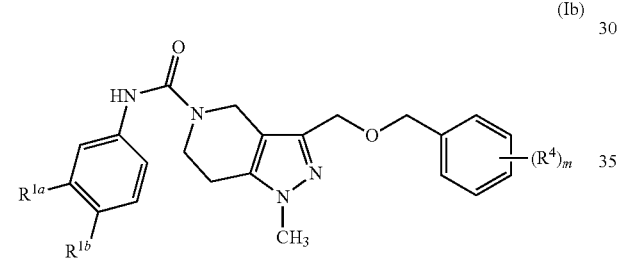

(Ib)

wherein, m is 0, 1 or 2;

$R^{1a}$ and $R^{1b}$ are the same or different and independently hydrogen, optionally substituted alkyl, optionally substituted alkoxy, halo, trifluoroalkyl, or optionally substituted thioalkyl; and each $R^4$ is the same or different and independently optionally substituted alkyl or halo.

In various embodiments, $R^{1a}$ and $R^{1b}$ are independently $C_1$-$C_4$ alkyl, $C_1$-$C_4$ alkoxy, $C_1$-$C_4$ thioalkyl, trifluoroalkyl, or halo. In more specific embodiments, $R^{1a}$ and $R^{1b}$ are the same or different and independently methyl, ethyl, methoxy, thiomethyl, fluoro or chloro.

In preferred embodiments, when $R^{1a}$ is hydrogen, $R^{1b}$ is $C_1$-$C_4$ alkyl, $C_1$-$C_4$ alkoxy, $C_1$-$C_4$ thioalkyl or halo. In more specific embodiments, when $R^{1a}$ is hydrogen, $R^{1b}$ is methyl, ethyl, methoxy, or chloro.

In other embodiments, when $R^{1b}$ is hydrogen, $R^{1a}$ is $C_1$-$C_4$ alkyl, $C_1$-$C_4$ alkoxy, $C_1$-$C_4$ thioalkyl, trifluoroalkyl, or halo. In more specific embodiments, when $R^{1b}$ is hydrogen, $R^{1a}$ is methyl, ethyl, methoxy, fluoro, or chloro.

Table 2 provides specific compounds of Formula (Ib) and their respective percentage inhibition of human pendrin. These compounds also demonstrated strong inhibition (at least 45% inhibition) at 25 μM.

TABLE 2

| Compounds of Formula (Ib) | Inh. (%) |
|---|---|
| (structure with 3-chloro-4-methylphenyl urea and 3-fluorobenzyloxymethyl) | 49 |
| (structure with 3,4-dimethylphenyl urea and 2-chloro-4-fluorobenzyloxymethyl) | 48 |
| (structure with 4-ethylphenyl urea and 2-chloro-4-fluorobenzyloxymethyl) | 49 |
| (structure with 3,4-dimethylphenyl urea and 4-chlorobenzyloxymethyl) | 49 |

Yet another embodiment provides a pharmaceutical composition comprising a pharmaceutically acceptable excipient and a pyrazolothiophenesulfonamide compound represented by Formula (II):

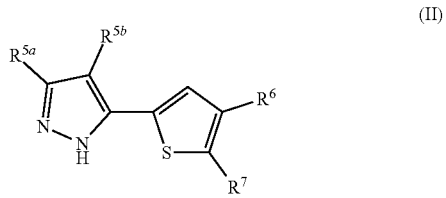

(II)

wherein, $R^{5a}$ and $R^{5b}$ are the same or different and independently hydrogen, or optionally substituted alkyl;

$R^6$ and $R^7$ are the same or different and independently hydrogen, optionally substituted alkyl, or —S(O)$_2$NHR, provided one of $R^6$ and $R^7$ is —S(O)$_2$NHR; and R is optionally substituted aryl or optionally substituted cycloalkyl.

In various embodiments, $R^{5a}$ and $R^{5b}$ are the same or different and independently hydrogen or methyl.

In other embodiments, $R^6$ is —S(O)$_2$NHR, and $R^7$ is hydrogen or methyl.

In yet other embodiments, $R^7$ is —S(O)$_2$NHR, and $R^6$ is hydrogen or methyl.

In various embodiments, R is optionally substituted aryl. In a particularly preferred embodiment, R is tetrahydronaphthalenyl (e.g., 1-tetrahydronaphthalenyl)

In other embodiments, R is phenyl optionally substituted by one or more alkyl (e.g., methyl or ethyl).

In further embodiments, R is optionally substituted cycloalkyl, including for example, cyclohexyl and cyclopentyl.

Table 3 provides specific compounds of Formula (II) and their respective percentage inhibition of human pendrin. These compounds also demonstrated strong inhibition (at least 45% inhibition) at 25 µM.

TABLE 3

| Compounds of Formula (II) | Inh (%) |
|---|---|
| 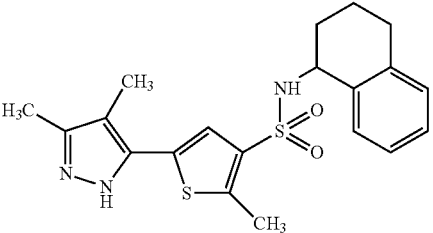 PDS$_{inh}$-C01 | 83 |
| 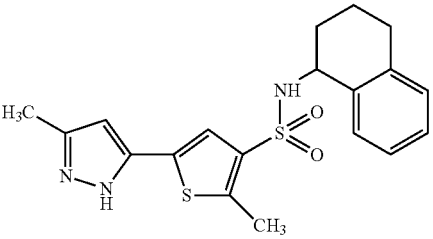 | 53 |
| 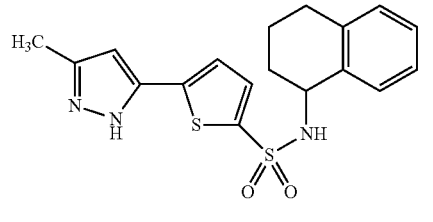 | |

The small molecule pendrin inhibitors of Formulae (I), (II) and substructures may be formulated into pharmaceutical composition by known methods in the art. The pharmaceutical composition additionally comprises a physiologically acceptable excipient (pharmaceutically acceptable or suitable excipient or carrier) (i.e., a non-toxic material that does not interfere with the activity of the active ingredient). Any suitable excipient or carrier known to those of ordinary skill in the art for use in pharmaceutical compositions may be employed in the compositions described herein. Excipients for therapeutic use are well known, and are described, for example, in *Remington: The Science and Practice of Pharmacy* (Gennaro, 21$^{st}$ Ed. Mack Pub. Co., Easton, Pa. (2005))

The pharmaceutical compositions disclosed herein may be a sterile aqueous or non-aqueous solution, suspension or emulsion. Such compositions may also be in the form of a solid, liquid, or gas (aerosol). Alternatively, compositions described herein may be formulated as a lyophilizate, or compounds may be encapsulated within liposomes using technology known in the art. Pharmaceutical compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

A composition comprising any one of the compounds described herein may be formulated for sustained or slow release. Such compositions may generally be prepared using well known technology and administered by, for example, oral, rectal or subcutaneous implantation, or by implantation at the desired target site.

In a preferred embodiment, the pharmaceutical compositions described herein may be used in aerosol formulation to be administered via inhalation. The compounds may be formulated into pressurized acceptable propellants such as dichlorodifluoromethane, propane, nitrogen and the like. The aerosol formulation is particularly suitable for delivering the pendrin inhibitors to the airways.

In another preferred embodiment, the pendrin inhibitor of the present disclosure can be combined with a loop diuretic (e.g., furosemide) in a pharmaceutical composition.

Treatment of Airway Diseases

In airway epithelial cells, pendrin is thought to facilitate Cl$^-$/HCO$_3^-$ exchange and may thereby affect the volume and composition of ASL. Inhibition of the pendrin activities in the airway epithelial cells is thus capable of regulating ASL volume, which could secondarily affect mucociliary clearance, bacterial colonization, and other mucosal immune responses associated with abnormal ASL volume.

Thus, one embodiment provides a method of treating an airway disease in a subject in need thereof comprising administering to the subject a therapeutically effective amount of a pharmaceutical composition having a compound of any one of Formulae (I), (Ia), (Ib) or Formula (II).

As used herein, "airway diseases" is characterized by low or abnormal ASL volume and may have a range of symptoms, including mucus production, cough, wheezing, and airway hyper-responsiveness. Airway diseases may take the forms of inflammatory lung diseases (e.g., cystic fibrosis, asthma, and chronical obstructive pulmonary disease), rhinovirus infection, rhinitis, chronic rhinosinusitis, sinusitis, certain viral or bacterial infections, and exposure to industrial toxins.

As demonstrated in further detail in Example 6, the pendrin inhibitors disclosed herein are efficacious in increasing ASL volume and improve ASL hydration in airway cell culture subjected to an inflammatory stimulant (IL-13). Increased airway hydration by pendrin inhibition represents a viable treatment of inflammatory lung diseases including CF. Although pendrin activity and increased ASL hydration were seen only in cell cultures after IL-13-treatment, asthma-like symptoms (cough, wheezing, airway hyper-responsiveness) and increased IL-13 are prevalent in subjects with CF, as well as other airway diseases.

Thus, a specific embodiment provides a method of treating cystic fibrosis in a subject in need thereof comprising administering to the subject a therapeutically effective amount of a pharmaceutical composition having a compound of any one of Formulae (I), (Ia), (Ib) or Formula (II).

In still other embodiments, the present disclosure provides methods for treating a disease or condition treatable by inhibiting pendrin, partially or completely, in a subject, the method comprising administering a pharmaceutical composition comprising a pharmaceutically acceptable excipient and any one or more of the foregoing compounds of Formula (I), (Ia), (Ib) or Formula (II) to the subject.

In the context of inhibiting pendrin, i.e., pendrin-mediated anion exchange, "inhibit" refers specifically to a statistically significant reduction or a decrease in pendrin-mediated anion exchange between a cell and its local environment, relative to a reference. Pendrin inhibition by the compounds of Formula (I), (Ia), (Ib) or (II) can be assessed, at a given molar amount, in human pendrin. As used herein, the molar amount of the pendrin inhibitor may be 2.5 µM, 10 µM or 25 µM. The compounds of Formula (I), (Ia), (Ib) or (II) disclosed herein typically exhibit percentage inhibition (at 25 µM) of at least 45%, or at least 50%, or at least 60%, or at least 70%, or at least 80% or at least 90% or fully blocking the pendrin activity (near 100% for $PDS_{inh}$-A01). Without wishing to be bound by theory, pendrin-mediated anion exchange may be inhibited by impairing an anion-exchange functionality of pendrin, by reducing or decreasing pendrin protein expression, by reducing or decreasing pendrin protein translation, or by reducing or decreasing pendrin gene expression. Compounds of the present disclosure may be said to be "pendrin-inhibiting" as well as "inhibiting pendrin-mediated anion exchange". These phrases are intended to carry the same meaning; compounds of the present disclosure inhibit the ability of pendrin to perform or facilitate anion exchange.

Treatment of Hypertension

Hypertension, also known as high blood pressure, is a long-term medical condition in which the blood pressure in the arteries is persistently elevated. Hypertension is classified as either primary (essential) hypertension or secondary hypertension. Most cases are categorized as primary hypertension, which is defined as high blood pressure with no apparent underlying cause. The remaining cases (5-10%) are categorized as secondary hypertension, which is associated with an identifiable cause, such as narrowing of the aorta or kidney arteries, chronic kidney disease, or an endocrine disorder such as excess aldosterone, cortisol, or catecholamines.

Both primary hypertension and secondary hypertension are linked with ionic imbalances. For example, considerable evidence suggests that disturbances in renal salt/water balance (particularly in the intrarenal renin-angiotensin system) may account for increased resistance to blood flow. Similarly, secondary hypertension is commonly associated with kidney diseases such as renal stenosis. In another example, Liddle's syndrome, a rare inherited form of hypertension, is caused by mutations that affect sodium reabsorption in the renal distal tubule. Additionally, mice overexpressing pendrin have been shown to be hypertensive. Accordingly, pendrin inhibitors disclosed herein may be effective in treating one or more forms of hypertension, such as, for example, salt-sensitive hypertension.

Thus, a further embodiment provides a method for treating hypertension in a subject in need thereof comprising administering to the subject a therapeutically effective amount of a pharmaceutical composition having a compound of any one of Formulae (I), (Ia), (Ib) or Formula (II).

Treatment of Thyroid Conditions

Ionic imbalance has also been associated with thyroid issues, including goiter, nodules, tumors, and aberrant thyroid activity. For example, elevated anion gap, which is the difference between measured cation and anion levels in serum, plasma, or urine, has been investigated for association with thyroid dysfunction and nodular goiter. Metabolic acidosis, caused by excessive production of acid and/or deficient removal of acid by the kidneys, is found among patients experiencing hypo- or hyperthyroidism. Thus, pendrin inhibitors disclosed herein may be effective in treating thyroid conditions.

One embodiment provides a method of treating thyroid conditions in a subject in need thereof comprising administering to the subject a therapeutically effective amount of a pharmaceutical composition having a compound of any one of Formulae (I), (Ia), (Ib) or Formula (II).

Diuresis and Potentiation

Pendrin inhibitors disclosed herein may be combined with diuretic therapy to enhance diuresis and salt excretion. Such a combination therapy can be effective in treating hypertension and edema (including diuretic-resistant edema).

Diuresis is the physiological process by which urine production in the kidneys is increased as part of the body's homeostatic maintenance of fluid balance. A diuretic promotes urine output, osmolality and salt excretion. Although pendrin inhibitors disclosed herein do not appear to be diuretic in an animal model, when combined with a known loop diuretic, the pendrin inhibitors can enhance or potentiate the effect of the loop diuretic (e.g., urine output and $Na^+$ secretion were increased by more than 30%, or by more than 60% depending on the use of the diuretic).

Thus, one embodiment provides a method of promoting diuresis to a subject in need thereof comprising administering to the subject a diuretic; and administering to the subject a pendrin inhibitor of any one of Formula (I), (Ia), (Ib) or (II). The pendrin inhibitor may be administered prior to, contemporaneous with, or following administration of the diuretic to the subject. In various embodiments, the diuretic may be administered to the subject acutely or chronically.

As used herein, a diuretic refers to a loop diuretic, which acts on the $Na^+/K^+/2Cl^-$ cotransporter (NKCC2) in the thick ascending limb of the loop of Henle to inhibit sodium, chloride and potassium reabsorption. Common loop diuretics include thiazide compounds such as furosemide, azosemide, bumelanide, piretanide, torasemide, and the like. In a preferred embodiment, the loop diuretic is furosemide.

Another embodiment provides a method for treating hypertension in a subject in need thereof comprising administering to the subject a diuretic; and administering to the subject a pendrin inhibitor of any one of Formula (I), (Ia), (Ib) or (II).

Another embodiment provides a method for treating edema in a subject in need thereof comprising administering to the subject a diuretic; and administering to the subject a pendrin inhibitor of any one of Formula (I), (Ia), (Ib) or (II).

Definitions

The terms below, as used herein, have the following meanings, unless indicated otherwise.

"Alkyl" refers to a straight or branched hydrocarbon chain radical which is saturated having from one to 12 carbon atoms, and which is attached to the rest of the molecule by a single bond. An alkyl comprising up to 12 carbon atoms is referred to as a $C_1$-$C_{12}$ alkyl. Alkyls comprising other numbers of carbon atoms are represented similarly. Alkyl groups include, but are not limited to, $C_1$-$C_{12}$ alkyl, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (iso-propyl), n-butyl, i-butyl, s-butyl, n-pentyl, 1,1-dimethylethyl (t-butyl), 3-methylhexyl, 2-methylhexyl, and the like. Unless stated otherwise specifically in the specification, an alkyl group may be optionally substituted as described below.

"Alkylene" or "alkylene chain" refers to a straight or branched divalent hydrocarbon chain linking the rest of the molecule to a radical group. Alkylenes may be saturated or unsaturated (i.e., contains one or more double and/or triple bonds). Representative alkylenes include, but are not limited to, $C_1$-$C_{12}$ alkylene, $C_1$-$C_8$ alkylene, $C_1$-$C_6$ alkylene, $C_1$-$C_4$ alkylene, $C_1$-$C_3$ alkylene, $C_1$-$C_2$ alkylene, $C_1$ alkylene. Representative alkylene groups include, but are not limited to, methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted as described below.

"Alkoxy" refers to a radical of the formula —OR$_a$ where R$_a$ is an alkyl radical as defined. Alkoxy groups include, but are not limited to, $C_1$-$C_2$ alkoxy, $C_1$-$C_{10}$ alkoxy, $C_1$-$C_8$ alkoxy, $C_1$-$C_6$ alkoxy, $C_1$-$C_4$ alkoxy, $C_1$-$C_3$ alkoxy, $C_1$-$C_2$ alkoxy, $C_2$-$C_8$ alkoxy, $C_3$-$C_8$ alkoxy and $C_4$-$C_8$ alkoxy. Unless stated otherwise specifically in the specification, an alkoxy group (i.e., the alkyl portion) may be optionally substituted as described below.

"Alkoxyalkyl" refers to a radical of the formula —R$_b$OR$_a$ where R$_a$ is an alkyl radical as defined and where R$_b$ is an alkylene radical as defined. Unless stated otherwise specifically in the specification, an alkoxyalkyl group may be optionally substituted as described below.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. Aryl radicals include, but are not limited to, aryl radicals derived from the hydrocarbon ring systems of aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. As used herein, it is not required that the aryl radical is fully aromatic (i.e., with fully unlocalized electrons). Instead, the aryl radical comprises at least one aromatic ring, which may be fused to a non-aromatic ring. An example is tetrahydronaphthalene. Unless stated otherwise specifically in the specification, the term "aryl" or the prefix "ar-" (such as in "aralkyl") is meant to include aryl radicals that are optionally substituted.

"Aralkyl" refers to a radical of the formula —R$_b$-R$_c$ where R$_b$ is an alkylene chain as defined above and R$_c$ is one or more aryl radicals as defined above, for example, benzyl, diphenylmethyl, trityl and the like. Unless stated otherwise specifically in the specification, an aralkyl group, i.e., the aryl moiety, may be optionally substituted.

"Cycloalkyl" refers to a stable 3-10 member non-aromatic ring radical comprising solely of carbon and hydrogen. The cycloalkyl radical may be a monocyclic, bicyclic, tricyclic or tetracyclic ring system, which may include fused or bridged ring systems. Examples of cycloalkyl radicals include, but are not limited to, cyclohexyl, cyclopentyl. Unless stated otherwise specifically in the specification, a cycloalkyl group may be optionally substituted.

"Halo" or "halogen" refers to bromo (Br), chloro (Cl), fluoro (F) or iodo (I).

"Haloalkyl" refers to an alkyl substituted with one or more halo, for example, trifluoroalkyl, wherein at three hydrogen atoms have been replaced with fluoro moieties. Trifluoroalkyls include trifluoromethyl and the like.

"Heterocyclyl", "heterocycle" or "heterocyclic ring" refers to a stable 3- to 24-membered non-aromatic ring radical comprising 2 to 23 carbon atoms and from one to 8 heteroatoms selected from the group consisting of nitrogen, oxygen, phosphorous and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 12-crown-4,15-crown-5,18-crown-6,21-crown-7, aza-18-crown-6, diaza-18-crown-6, aza-21-crown-7, and diaza-21-crown-7. Unless stated otherwise specifically in the specification, a heterocyclyl group may be optionally substituted.

"Heterocyclylalkyl" refers to a radical of the formula —R$_b$-R$_c$ where R$_b$ is an alkylene chain as defined above and R$_c$ is one or more heterocyclyl radicals as defined above, for example, tetrahydrofuranyl-methyl, tetrahydropyranylmethyl and the like. A 6-membered heterocyclylalkyl refers to a heterocyclylalkyl, wherein the heterocyclyl moiety has 6 atoms in the ring. Unless stated otherwise specifically in the specification, a heterocycloalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

"Heteroarylalkyl" refers to a radical of the formula —$R_b$-$R_c$ where $R_b$ is an alkylene chain as defined above and $R_c$ is one or more heteroaryl radicals as defined above, for example, furanyl-methyl, pyridyl-methyl and the like. A 6-membered heteroarylalkyl refers to a heteroarylalkyl, wherein the heteroaryl moiety has 6 atoms in the ring. Unless stated otherwise specifically in the specification, a heteroarylalkyl group may be optionally substituted.

"Thioalkyl" refers to a radical of the formula —S—Ra where $R_a$ is an alkyl radical as defined. Thioalkyl groups include, but are not limited to, $C_1$-$C_{12}$ thioalkyl, $C_1$-$C_{10}$ thioalkyl, $C_1$-$C_8$ thioalkyl, $C_1$-$C_6$ thioalkyl, $C_1$-$C_4$ thioalkyl, $C_1$-$C_3$ thioalkyl, $C_1$-$C_2$ thioalkyl, $C_2$-$C_8$ thioalkyl, $C_3$-$C_8$ thioalkyl and $C_4$-$C_8$ thioalkyl. Unless stated otherwise specifically in the specification, a thioalkyl group (i.e., the alkyl portion) may be optionally substituted.

All the above groups may be "optionally substituted," i.e., either substituted or unsubstituted. The term "substituted" as used herein means any of the above groups (i.e., alkyl, alkylene, alkoxy, alkoxyalkyl, aryl, aralkyl, heterocyclyl, heterocyclylalkyl, heteroaryl, heteroarylalkyl and/or trifluoroalkyl), may be further functionalized wherein at least one hydrogen atom is replaced by a bond to a non-hydrogen atom substituent. Unless stated specifically in the specification, a substituted group may include one or more substituents selected from: oxo, —$CO_2H$, nitrile, nitro, —$CONH_2$, hydroxyl, thiooxy, alkyl, alkylene, alkoxy, alkoxyalkyl, alkylcarbonyl, alkyloxycarbonyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cycloalkyloxycarbonyl, heterocyclyl, heteroaryl, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, thioalkyl triarylsilyl groups, perfluoroalkyl or perfluoroalkoxy, for example, trifluoromethyl or trifluoromethoxy. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$CH_2SO_2R_g$, —$CH_2SO_2NR_gR_h$, —SH, —$SR_g$ or —$SSR_g$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. In addition, each of the foregoing substituents may also be optionally substituted with one or more of the above substituents.

The compounds described herein may generally be used as the free acid or free base. Alternatively, the compounds may be used in the form of acid or base addition salts. Acid addition salts of the free base amino compounds may be prepared according to methods well known in the art, and may be formed from organic and inorganic acids. Suitable organic acids include (but are not limited to) maleic, fumaric, benzoic, ascorbic, succinic, methanesulfonic, acetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include (but are not limited to) hydrochloric, hydrobromic, sulfuric, phosphoric, and nitric acids. Base addition salts of the free acid compounds of the compounds described herein may also be prepared by methods well known in the art, and may be formed from organic and inorganic bases. Suitable inorganic bases included (but are not limited to) the hydroxide or other salt of sodium, potassium, lithium, ammonium, calcium, magnesium, iron, zinc, copper, manganese, aluminum, and the like, and organic bases such as substituted ammonium salts. Thus, the term "pharmaceutically acceptable salt" of compounds of Structures I and II and substructures thereof, as well as any and all substructures and specific compounds described herein is intended to encompass any and all pharmaceutically suitable salt forms.

With regard to stereoisomers, the compounds of structure (I) and structure (II), as well as any sub-structure herein, may have one or more chiral (or asymmetric) centers, and may thus give rise to enantiomers, diastereomers, and other stereoisomeric forms that may be defined, in terms of absolute stereochemistry, as (R)- or (S)-. When the compounds described herein contain olefinic double bonds or other centers of geometric asymmetry, and unless specified otherwise, it is intended that the compounds include both E and Z geometric isomers (e.g., cis or trans.) Likewise, all possible isomers, as well as their racemic and optically pure forms, and all tautomeric forms are also intended to be included. It is therefore contemplated that various stereoisomers and mixtures thereof and includes "enantiomers," which refers to two stereoisomers whose molecules are nonsuperimposable mirror images of one another. Thus, the compounds may occur in any isomeric form, including racemates, racemic mixtures, and as individual enantiomers or diastereomers.

Furthermore, some of the crystalline forms of any compound described herein may exist as polymorphs, which are also included and contemplated by the present disclosure. In addition, some of the compounds may form solvates with water or other organic solvents. Such solvates are similarly included within the scope of compounds and compositions described herein.

As used herein, "administer," "administering," or "to administer" refers to the giving or supplying of a medication, including in vivo administration, as well as administration directly to tissue ex vivo. Generally, compositions may be administered systemically orally, bucally, parenterally, topically, by inhalation or insufflation (i.e., through the mouth or through the nose) or rectally in dosage unit formulations containing conventional nontoxic pharmaceutically acceptable carriers, adjuvants and vehicles as desired, or may be locally administered by means such as, but not limited to, injection, implantation, grafting, topical application or parenterally.

The terms "agent" and "therapeutic agent" are used interchangeably herein to refer to a drug, molecule, composition, or other substance that provides a therapeutic effect. The term "active agent" as used herein, refers to the ingredient, component or constituent of the compositions of the described invention responsible for the intended therapeutic effect.

As used herein, the term "treat," "treating," or "to treat" as used herein, refers to accomplishing one or more of the following: (a) reducing the severity of a disorder; (b) limiting the development of symptoms characteristic of a disorder being treated; (c) limiting the worsening of symptoms characteristic of a disorder being treated; (d) limiting the recurrence of a disorder in patients that previously had the disorder; and I limiting recurrence of symptoms in patients that were previously asymptomatic for the disorder. The term "treat", "treating" or "to treat" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms.

The term "about" when referring to a number or a numerical range means that the number or numerical range referred to is an approximation within experimental variability (or within statistical experimental error), and thus the number or numerical range may vary between 1% and 15% of the stated number or numerical range. It should also be noted that the term "or" is generally employed in its sense including "and/or" unless the content clearly dictates otherwise.

Methods of Using Pharmaceutical Compositions

In pharmaceutical dosage forms, any one or more of the compounds of Formula (I), (Ia), (Ib) or (II), substructures, and specific structures described herein may be administered in the form of a pharmaceutically acceptable derivative, such as a salt, or they may also be used alone or in appropriate association, as well as in combination, with other pharmaceutically active compounds. An effective amount or therapeutically effective amount refers to an amount of a compound or a composition comprising one or more compounds administered to a subject, either as a single dose or as part of a series of doses, which is effective to produce a desired therapeutic effect.

Optimal doses may generally be determined using experimental models and/or clinical trials. The optimal dose may depend upon the body mass, weight, or blood volume of the subject. In general, the amount of a compound described herein, that is present in a dose, ranges from about 0.01 µg to about 1000 µg per kg weight of the host. The use of the minimum dose that is sufficient to provide effective therapy is usually preferred.

Pharmaceutical compositions may be administered in a manner appropriate to the disease or disorder to be treated as determined by persons skilled in the medical arts. Generally, compositions may be administered systemically orally, bucally, parenterally, topically, by inhalation or insufflation (i.e., through the mouth or through the nose). For airway diseases, the pharmaceutical composition disclosed herein may be administered directly into the airway. For diuretic combination therapy, the, the pharmaceutical composition disclosed herein may be administered orally.

The diuretic combination therapy may be administered concurrently when the pendrin inhibitors of Formula (I), (Ia), (Ib) or (II) are formulated into the same pharmaceutical composition with the diuretic or into separate pharmaceutical compositions.

The diuretic combination therapy may be administered in sequential administration, whereby the pendrin inhibitors may be administered by the same route or by different routes from that of the diuretic.

Other embodiments and uses will be apparent to one skilled in the art in light of the present disclosures. The following examples are provided merely as illustrative of various embodiments and shall not be construed to limit the claims in any way.

EXAMPLES

Example 1

High-Throughput Identification of Small Molecule Pendrin Inhibitors

Cells for High-Throughput Screening

Fischer rat thyroid (FRT) cells were cultured in Kaign's modified Ham's F12 medium supplemented with 10% FBS, 2 mM L-glutamine, 100 U/ml penicillin, 100 mg/ml streptomycin, 18 mg/ml myo-inositol and 45 mg/ml ascorbic acid. For high-throughput screening, FRT cells were stably transfected with EYFP-H148Q/I152L/F46L (EYFP-HIF; in pcDNA3.1/Hygro (+)), isolated using 0.25 mg/ml hygromycin B, and then transfected with pcDNA3.1 (+) encoding human pendrin with clonal cell lines selected using 0.5 mg/ml G418.

Human Bronchial Epithelial Cell Cultures

Bronchial tissues were obtained from non-CF (without significant airway disease) and CF subjects following lung transplantation, or from lungs donated for transplantation but subsequently found to be unsuitable for that purpose. Non-CF and CF human bronchial epithelial (HBE and CFBE, respectively) cell cultures were grown at an air-liquid interface as described in detail. At 21 days post-seeding, cells typically formed a tight epithelium ($R_{TE}$>1000 $\Omega cm^2$). In some experiments, the culture medium was supplemented with 10 ng/ml recombinant human IL-13 (Peprotech, Rocky Hill, N.J.) for 7 days starting at day 21 of culture. As needed, the apical cell surface was rinsed with PBS to remove excess mucus 24 hours or more before ASL measurements. Pendrin transcript levels in human primary cells were measured by Taqman quantitative PCR using the Hs00166504_m1 probe set (ThermoFisher Scientific, Grand Island, N.Y.) at the UCSF Helen Diller Cancer Center Genome Analysis Core. Human tissues were acquired and used with approval from the University of California, San Francisco Committee on Human Research.

Screening Procedures

High-throughput screening was performed using a semi-automated screening platform (Beckman, Fullerton, Calif.) configured as described. FRT cells expressing human pendrin and EYFP-HIF were plated in 96-well black-walled, clear-bottom tissue culture plates (Corning, Corning, N.Y.) at a density of 20,000 cells/well, and cultured to confluence over 48 h. For screening, plates were washed twice with PBS (in mM: 137 NaCl, 2.7 KCl, 1.1 $KH_2PO_4$, 8.1 $Na_2HPO_4$, 0.9 $CaCl_2$, 0.5 $MgCl_2$) prior to addition of 100 µl PBS containing test compounds. Screening was done with ~36,000 compounds from ChemDiv (San Diego, Calif.), TimTec (Newark, Del.), and Asinex (Winston-Salem, N.C.). After 10 min incubation with test compound, plates were transferred to a Tecan Infinite M1000 plate reader (Tecan, Morrisville, N.C.) for fluorescence assay of pendrin activity. The assay duration was 10 s with initial fluorescence intensity recorded for 2 s prior to addition of 100 µl of NaSCN-substituted PBS (137 mM NaCl replaced with NaSCN). All assay plates contained negative controls (DMSO). In some experiments Cl⁻ exchange for I⁻ or $NO_3^-$ was measured similarly using NaI and $NaNO_3$-substituted PBS. Control experiments to measure basal ion transport rates were done in FRT cells expressing EYFP-HIF without pendrin.

Figure 1D:
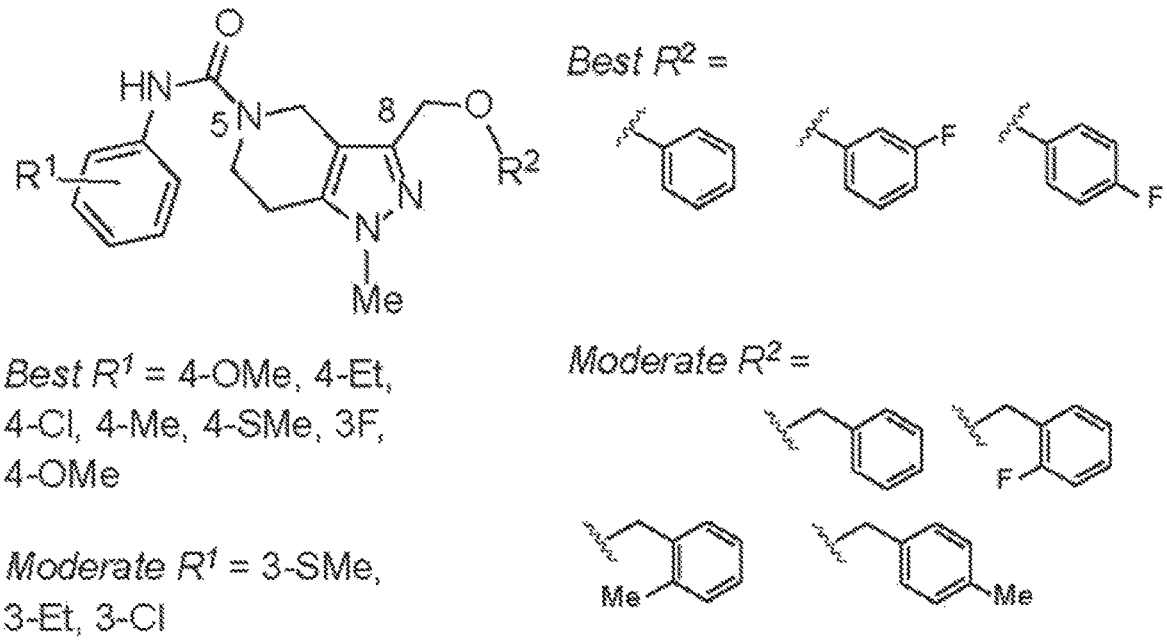
Figure 1D:
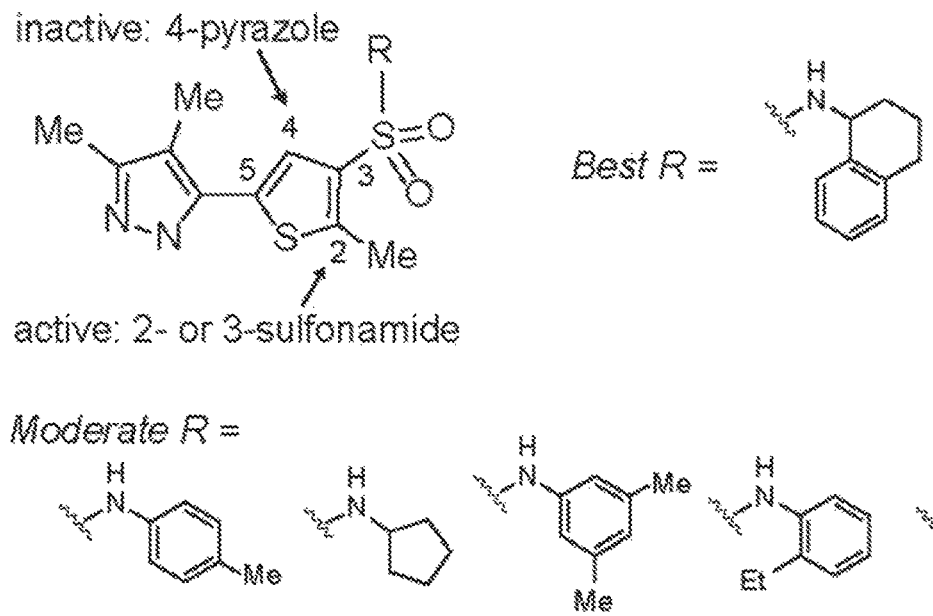

Screening of ~36,000 compounds produced several classes of compounds that inhibited pendrin by >50% at 25 µM (FIG. 1C). Based on their potency two compound classes (A and C) were further characterized. A total of 188 commercially available class A (tetrahydropyrazolopyridines) analogs and 160 class C (pyrazolothiophenesulfonamide) analogs were tested, with structural determinants of activity summarized in FIG. 1D.

Compounds of Formula (I) ("class A inhibitors") contained a core tetrahydropyrazolopyridine heterocycle with a substituted aniline linked to the core ring at the 5-position via a carbamate linker, and with a substituted-methoxy linked at the 8-position of the core. Analogs with different substitution on the aniline ring ($R^1$) were explored. Para-substituted aniline gave best activity whereas ortho-substitution (including methyl, methoxy, halo, and trifluoromethyl substituents) abolished activity. The electronic property of the substituent on the aniline appeared to be less crucial, with electron-donating and neutral groups giving highest activity. Several $R^2$ groups on the 8-methoxy were also explored. In general, analogs with $R^2$ substituted with phenyl rings were more active than with benzyl rings. Halide-substituted benzyl rings greatly reduced activity.

Compounds of Formula (II) ("class C inhibitors") are comprised of a thiophene with a sulfonamide group and a pyrazole heterocycle linked at the 3- and 5-positions, respectively. Changing the pyrazole from 5- to 4-position of the thiophene ring abolished activity. The sulfonamide group at the 2- or 3-position was tolerated. Substitution on the sulfonamide influenced activity, with primary sulfonamide bearing a bicyclic tetrahydronaphthalene ring giving best activity, whereas monocyclic ring or alkyl-substituted anilines generally reducing activity. Secondary sulfonamide, alkyl amines and electron-rich anilines had no activity. The most potent pendrin compound from each class, $PDS_{inh}$-A01 and $PDS_{inh}$-C01 (FIG. 1C, top), were further studied.

Example 2

$PDS_{Inh}$-A01 and $PDS_{Inh}$-C01 Reversibly Inhibit Pendrin-Mediated Anion Exchange Cytoplasmic pH ($pH_i$) was measured to assay pendrin-mediated $Cl^-/HCO_3^-$ exchange in pendrin-expressing FRT cells and primary cell cultures using the pH-sensitive fluorescent probe BCECF. Cells were loaded for 20 min using 10 µM BCECF-AM (Invitrogen, Carlsbad, Calif.) in $HCO_3^-$-containing buffer (in mM: 120 NaCl, 5 KCl, 1 $CaCl_2$), 1 $MgSO_4$, 10 glucose, 5 Hepes, 25 $NaHCO_3$; pH 7.4) at 27° C. in a tissue culture incubator. Cells were washed and transferred to the stage of a TE2000 microscope (Nikon, Melville, N.Y.) equipped with a C9100 EM-CCD (Hamamatsu, San Jose, Calif.), XCite light source (Excelitas, Waltham, Mass.), Nikon 20×N.A. 0.75 S Fluor objective, Uniblitz shutter (Vincent Associates, Rochester, N.Y.), and filters for BCECF fluorescence (Chroma, Bellows Fall, Vt.), where they were purged with 95% $O_2$/5% $CO_2$. Pendrin-mediated $Cl^-/HCO_3^-$ exchange was initiated by apical addition of $Cl^-$-free $HCO_3^-$-containing buffer (Na gluconate replacing NaCl; pH 7.4; 95% $O_2$/5% $CO_2$ equilibrated) to generate a 100 mM gluconate gradient driving cytoplasmic Cl⁻ efflux. BCECF pH-sensitive fluorescence (490 nm excitation, 535 nm emission) was acquired at 0.5 Hz, with control experiments confirming that BCECF pH-insensitive fluorescence was not altered during exchange protocols. In some experiments $pH_i$ changes in the absence of $HCO_3^-$ were measured using buffers in which NaCl or Na gluconate replaced $NaHCO_3^-$. To relate BCECF fluorescence to pH, a calibration curve over the quasi-linear range of BCECF sensitivity (pH 6.6-7.7) was generated as described.

Figure 2A:
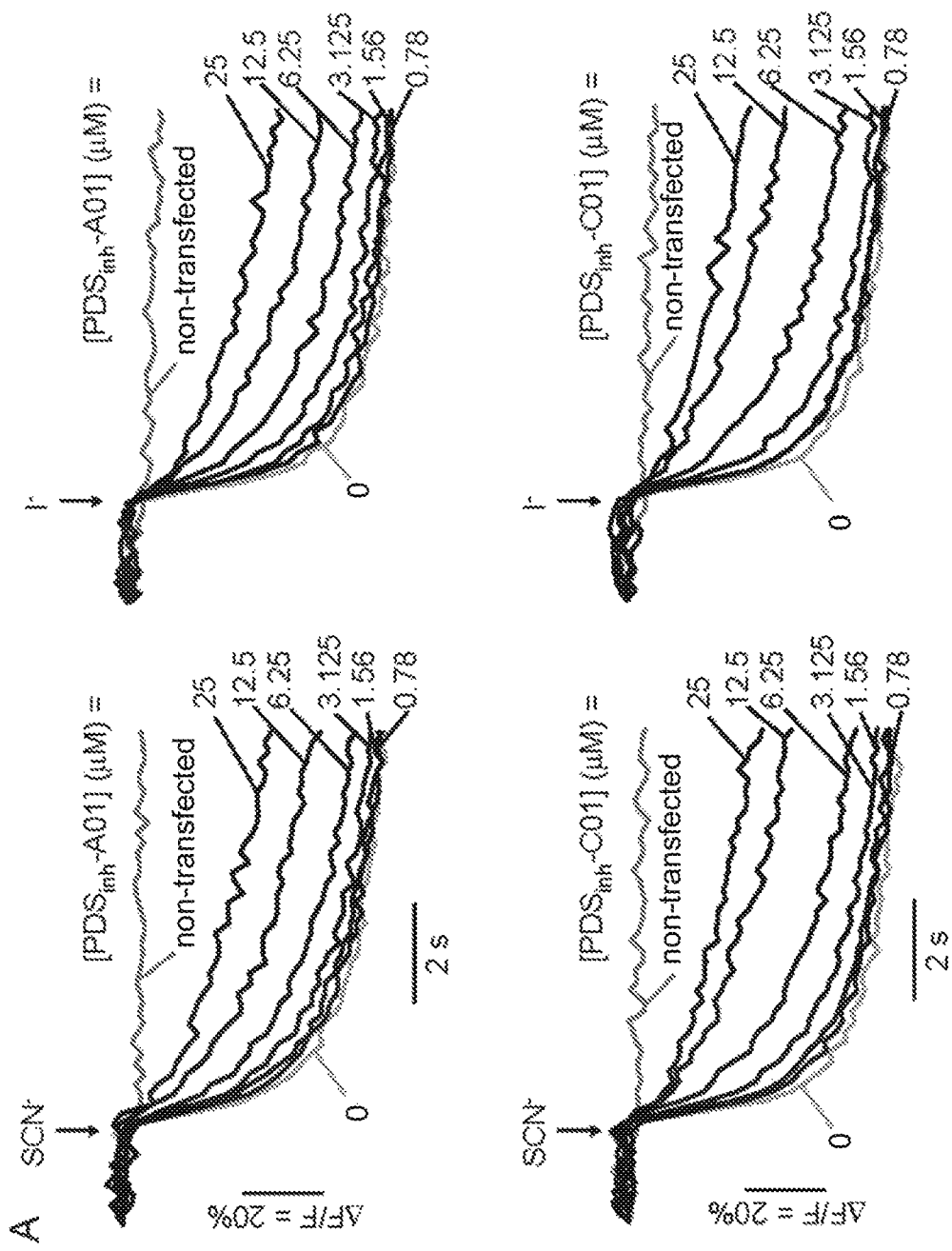
FIGS. 2A-2D present data illustrating kinetics of PDS$_{inh}$-A01 and PDS$_{inh}$-C01 inhibiting pendrin-mediated anion exchange.
Figure 2B:
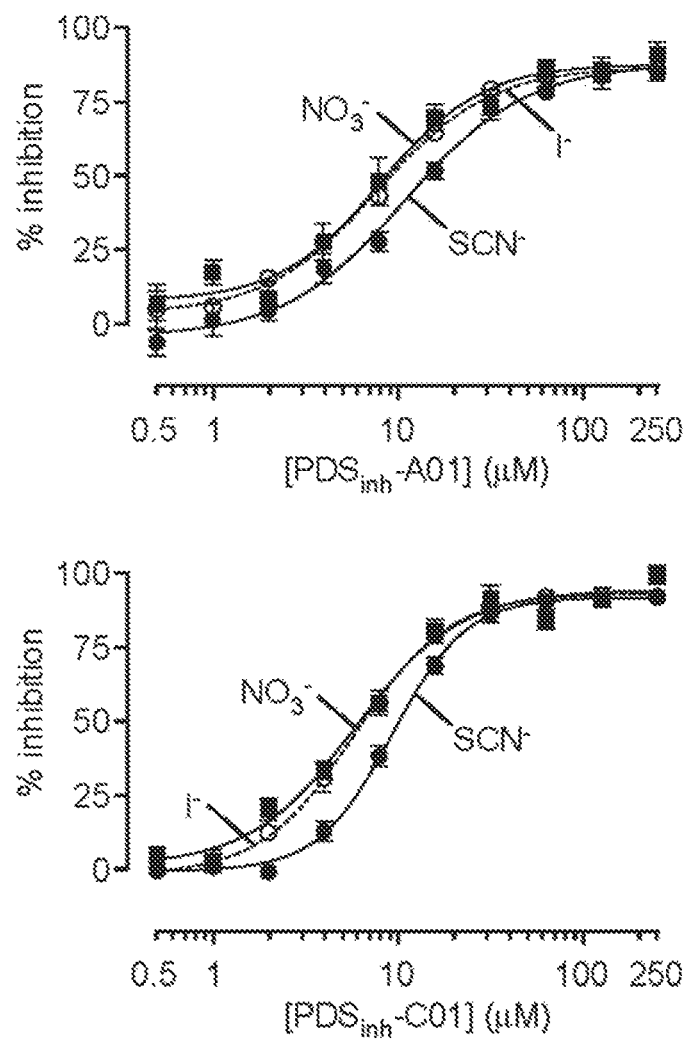

FRT cells were chosen for screening due to their low intrinsic permeability to anions that are transported by pendrin. As depicted in FIGS. 1A and 2A, pendrin activity was assayed from the kinetics of the halide-sensitive fluorescent protein EYFP-HIF in response to addition of a $SCN^-$-containing solution to drive pendrin-mediated $Cl^-/SCN^-$. Pendrin inhibition reduces the rate of EYFP-HIF quenching. $PDS_{inh}$-A01 land $PDS_{inh}$-C01 decreased pendrin-mediated $Cl^-/SCN^-$ and $Cl^-/I^-$ exchange in a concentration-dependent manner, as measured by YFP fluorescence quenching. These data are summarized, along with inhibition of $Cl^-/NO_3^-$ exchange, in FIG. 2B, together with data from a negative control (DMSO vehicle). Because the only previously-described pendrin inhibitor is the weakly active compound niflumic acid, no positive control was included in the screening plates.

Figure 2C:
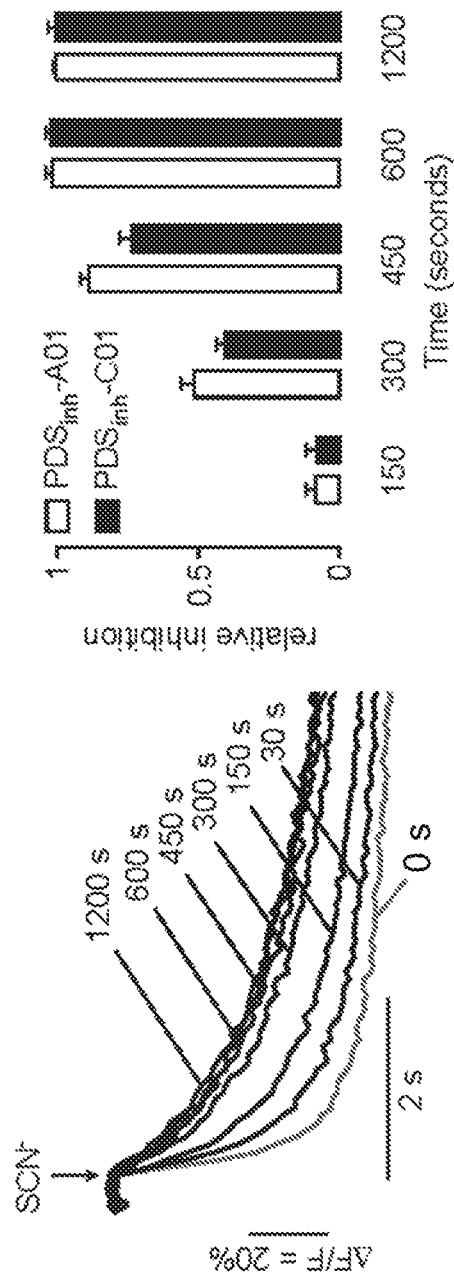
Figure 2D:
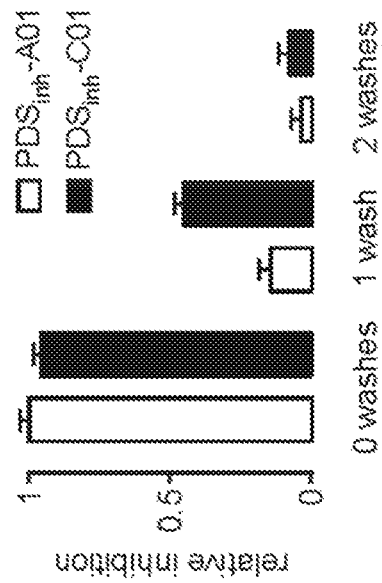

$IC_{50}$ values for $Cl^-/SCN^-$ exchange for both compounds were ~9 µM. $PDS_{inh}$-A0 land $PDS_{inh}$-C01 inhibited $Cl^-/I^-$ and $Cl^-/NO_3^-$ exchange with $IC_{50}$ of ~8 µM and ~5 µM, respectively. As shown in FIG. 2C, kinetics of $PDS_{inh}$-A01 and $PDS_{inh}$-C01 inhibition of pendrin-mediated $Cl^-/SCN^-$ exchange in which 10 µM $PDS_{inh}$-A01 was added for indicated times were measured (left). At right is a summary of these data in bar graph form. Both $PDS_{inh}$-A01 and $PDS_{inh}$-C01 displayed ~$IC_{50}$ at 5 minutes, and displayed substantially higher IC values by 7.5 minutes. Inhibition by both compounds is reversible by washout, as shown in FIG. 2D.

Example 3

Figure 3B:
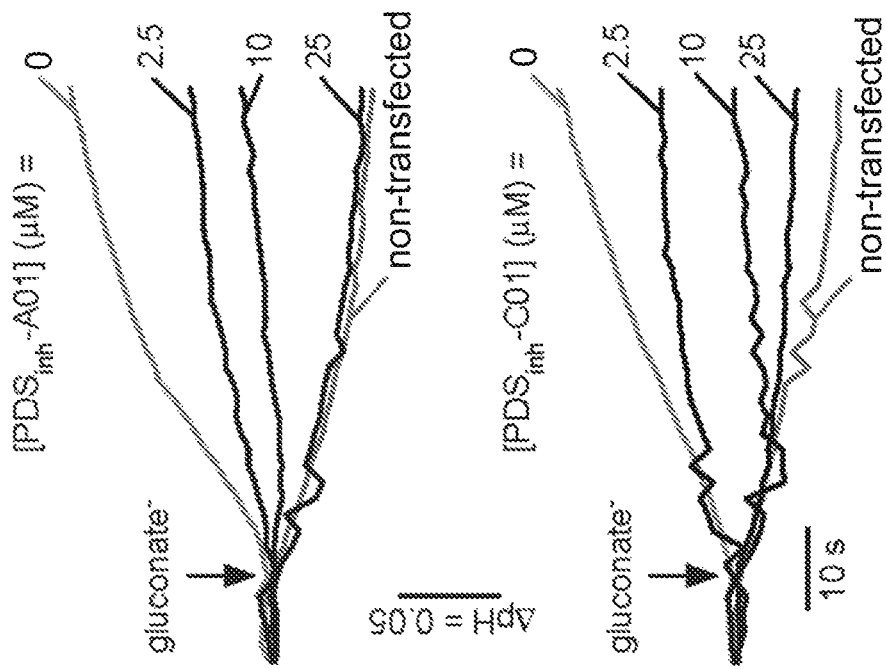
FIGS. 3A-3D illustrate pendrin inhibition by PDS$_{inh}$-A01 and PDS$_{inh}$-C01 and resultant effects on cytoplasmic pH.
Figure 3A:
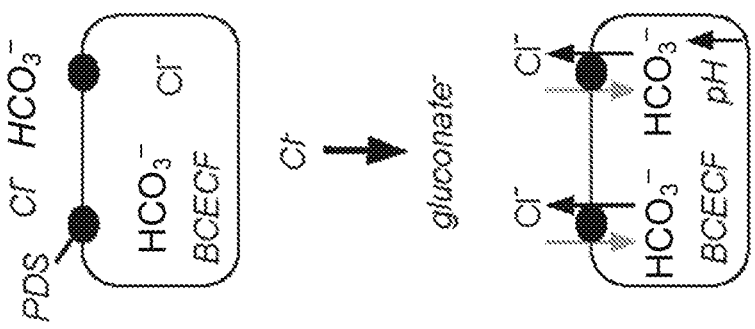
Figure 3C:
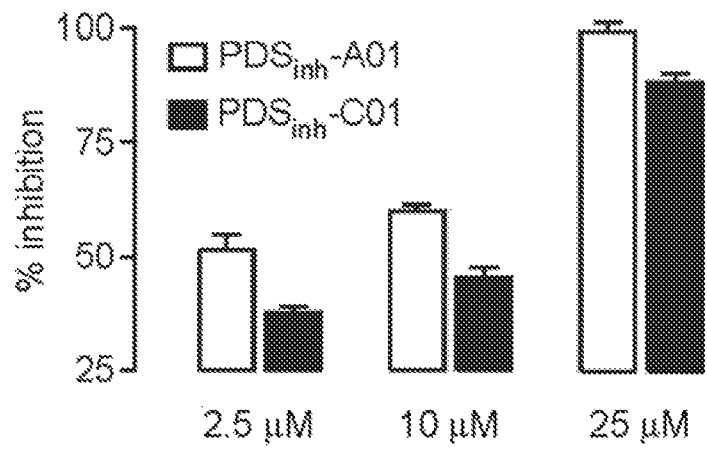
Figure 3D:
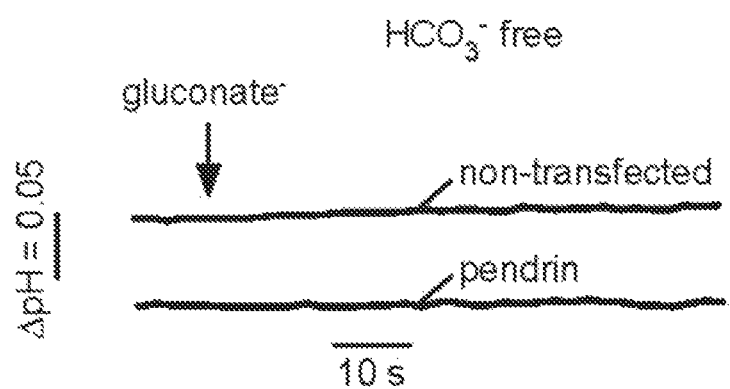

Pendrin Inhibitors Block $Cl^-/HCO_3^-$ Exchange $Cl^-/HCO_3^-$ exchange is the relevant pendrin function in the airways during inflammatory responses. Pendrin-mediated $Cl^-/HCO_3^-$ exchange was measured in pendrin-expressing FRT cells using BCECF to report cytoplasmic pH ($pH_i$) (FIG. 3A). BCECF-labeled cells were incubated in a $Cl^-$-containing $HCO_3^-$-buffered solution, and $Cl^-/HCO_3^-$ exchange was initiated by application of a gluconate-containing $HCO_3^-$-buffered solution to drive $Cl^-$ efflux and $HCO_3^-$ influx, producing cytoplasmic alkalinization with a rate of ~0.1 pH units per min (FIG. 3B). Cytoplasmic alkalinization was strongly inhibited by 25 µM $PDS_{inh}$-A01 or $PDS_{inh}$-C01, with the fluorescence responses similar to those in cells not expressing pendrin (FIG. 3B, top). Fifty percent inhibition was seen at ~2.5 µM $PDS_{inh}$-A01 (FIG. 3C). In control experiments done in the absence of $HCO_3^-$, application of the gluconate-containing solution to cells did not alter $pH_i$ in pendrin-expressing or non-transfected cells, indicating that observed pH changes are $HCO_3^-$-dependent, as expected (FIG. 3D).

Example 4

$PDS_{Inh}$-A01-Mediated Inhibition is Specific for Pendrin Ion Exchange Activity Over Other Solute Transport Proteins and Over the Sequence-Similar Slc26A3

Figure 4A:
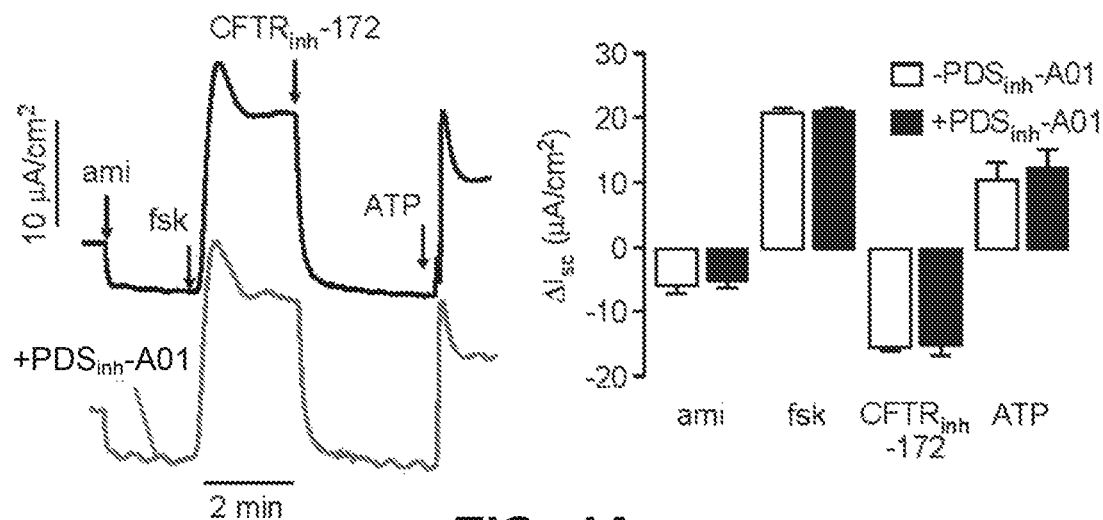
FIGS. 4A-4B illustrate PDS$_{inh}$-A01 selectivity for pendrin.

Further experiments were done with $PDS_{inh}$-A01 because of its greater inhibition potency for $Cl^-/HCO_3^-$ exchange than PDS$_{inh}$-C01. To investigate PDS$_{inh}$-A01 specificity, the major ion transport pathways in HBE cells were studied by short-circuit current ($I_{sc}$) analysis. Cells were treated with IL-13 to increase $Ca^{2+}$-activated $Cl^-$ conductance (CaCC) activity. For $I_{sc}$ measurements, cells were sequentially treated with amiloride to inhibit the epithelial sodium channel (ENaC), forskolin to activate the cystic fibrosis transmembrane conductance regulator (CFTR), CFTR$_{inh}$-172 to inhibit CFTR, and ATP to activate CaCC. In the absence of PDS$_{inh}$-A01, ion channel modulators produced the anticipated changes in $I_{sc}$ (FIG. 4A). Pre-treatment of cells for 30 min with 25 µM PDS$_{inh}$-A01 did not alter the $I_{sc}$ responses, indicating that PDS$_{inh}$-A01 did not affect the activity of ENaC, CFTR or CaCC, the various other transporters (including $K^+$ channels and NKCC1 cotransporter) required to support their activity, or tight junction conductance.

IL-13-treated HBE cells were cultured on Snapwell clear permeable supports (12 mm diameter, 0.4 µm polyester membrane, Costar, Corning, Corning, N.Y.). Short-circuit current was measured using symmetrical $HCO_3^-$-buffered solutions (in mM: 120 NaCl, 5 KCl, 1 $MgCl_2$, 1 $CaCl_2$, 5 Hepes, 25 $NaHCO_3$; pH 7.4) as described, with ion transport modulators added to both apical and basolateral bathing solutions. Cells were equilibrated with 95% $O_2$/5% $CO_2$ and maintained at 37° C. during data acquisition. Statistical analysis was by Student's t-test.

Figure 4B:
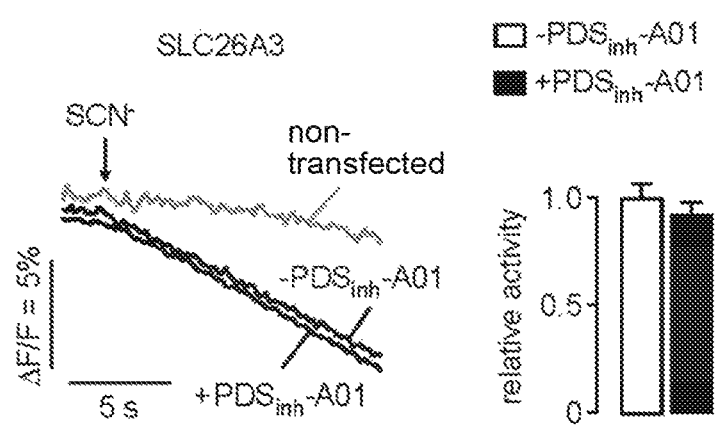

Experiments were also done to investigate PDS$_{inh}$-A01 effect on SLC26A3 (CLD (congenital chloride diarrhea)/DRA (downregulated in adenoma)), the protein most similar to pendrin in sequence (~50% identity). SLC26A3 activity was measured using a $SCN^-$ transport assay that produced YFP fluorescence quenching (FIG. 4B). YFP fluorescence quenching in SLC26A3-expressing cells in response to an $SCN^-$ gradient was not significantly inhibited by PDS$_{inh}$-A01.

SLC26A3-mediated ion transport was measured in COS7 fibroblasts transiently transfected to express EYFP-HIF and human SLC26A3 (Origene, Rockville, Md.). COS7 cells were cultured in DMEM-H21 supplemented with 10% FBS, 2 mM glutamine, 100 U/ml penicillin and 100 mg/ml streptomycin and transfected using Lipofectamine 2000 (Invitrogen, Carlsbad, Calif.). SLC26A3-mediated transport was measured from EYFP-HIF fluorescence after addition of a NaSCN-substituted PBS solution to generate a 70 mM $SCN^-$ gradient. Control experiments were done using COS-7 cells expressing EYFP-HIF alone.

Example 5

Figure 5A:
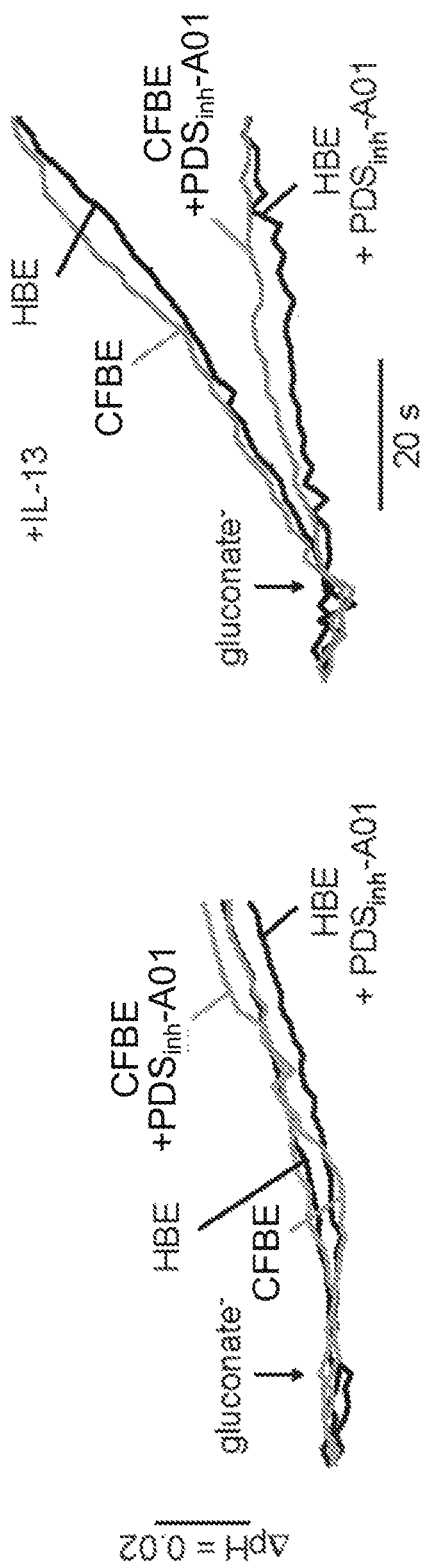
FIGS. 5A-5C present data indicating the effects of $PDS_{inh}$-A01 on $Cl^-/HCO_3^-$ exchange and ASL pH in untreated and IL-13-treated primary HBE and CFBE cell cultures.
Figure 5B:
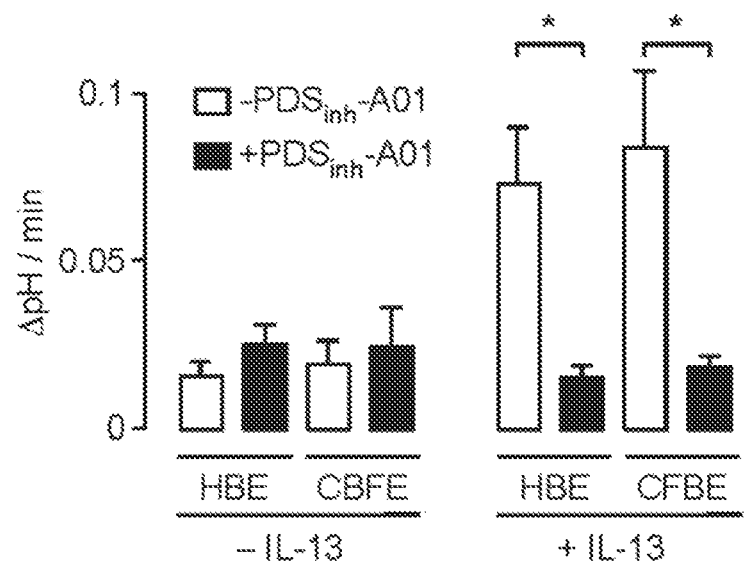

PDS$_{Inh}$-A01 Inhibits CL-/HCO3-Exchange in IL-13 Treated Primary Human Bronchial Epithelial Cell Cultures but does not Change ASL pH Pendrin-mediated $Cl^-/HCO_3^-$ exchange was measured in BCECF-labeled HBE and CFBE cells under basal conditions and after pendrin upregulation by IL-13, a cytokine that is elevated in multiple airway disease states including CF. In control cultures (no added IL-13) pH changes in response to apical application of a gluconate gradient to drive $Cl^-$ efflux and $HCO_3^-$ influx were not altered by PDS$_{inh}$-A01, suggesting little or no pendrin activity under basal conditions (FIG. 5A, left). However, treatment of cells with IL-13, which strongly upregulates pendrin expression, produced a robust intracellular alkalinization in response to a gluconate gradient, which was inhibited by 25 µM PDS$_{inh}$-A01 (FIG. 5A, right, data summary in FIG. 5B). Similar results were found in HBE and CFBE cultures. Quantitative PCR (qPCR) analysis indicated that pendrin transcript levels were increased by 30-35-fold in the HBE and CFBE cultures (data not shown), similar to fold-increases previously reported in similar cell systems.

Figure 5C:
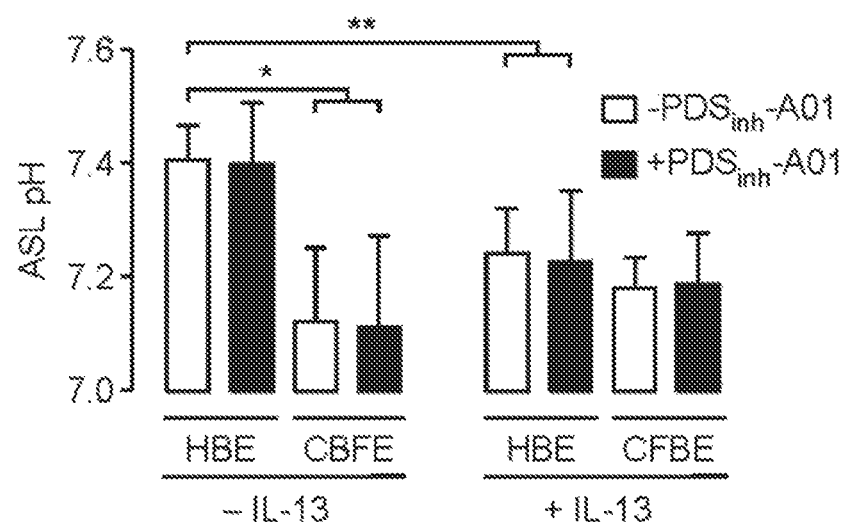

To investigate the possible involvement of pendrin in ASL pH regulation, fluorescence ratio imaging was done of the ASL in HBE and CFBE cultures after staining with BCECF-dextran. In the absence of IL-13-treatment, ASL pH was ~0.3 pH units more acidic in CFBE than HBE cultures (FIG. 5C; pH ~7.4 vs. ~7.1), in agreement with prior studies showing relative ASL acidity in CF. PDS$_{inh}$-A01 did not alter ASL pH under basal conditions. Treatment of HBE cell cultures with IL-13 produced a significant decrease in ASL pH by ~0.2 pH units, although no change in ASL pH was seen in IL-13-treated CF cultures. Incubation of IL-13-treated HBE and CFBE cell cultures with PDS$_{inh}$-A01 did not alter ASL pH. These studies indicate that pendrin is not a key determinant of ASL pH under basal or IL-13-stimulated conditions, suggesting that alternative pathways contribute to ASL pH homeostasis.

ASL pH was measured using the pH-sensitive fluorophore BCECF conjugated to 10 kDa dextran (Invitrogen, Carlsbad, Calif.) as described, which was added 4-6 h prior to measurement (20 µl of 0.5 mg/ml in PBS). Cell inserts were incubated in $HCO_3^-$-containing buffer (5% $CO_2$ environment) and the ASL was imaged using a SMZ stereoscopic microscope (Nikon, Melville, N.Y.) equipped with a C9100 EM-CCD, Exfo XCite light source and BCECF filters (440/10X, 490/20X, 535/25M, Chroma, Bellows Falls, Vt.). In some experiments ASL pH was measured after PDS$_{inh}$-A01 treatment, as described for ASL depth measurements. To relate BCECF fluorescence to pH, a calibration curve over the quasi-linear range of BCECF sensitivity was generated.

Example 6

Figure 6A:
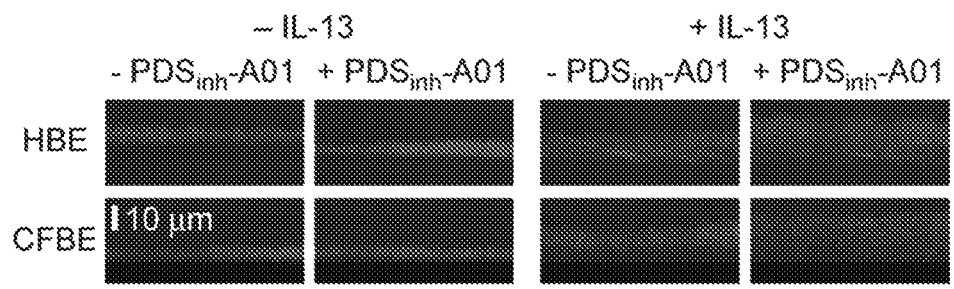
FIGS. 6A-6B present data demonstrating that IL-13 increases ASL depth in both primary HBE and CFBE cell cultures, and that pendrin inhibition significantly increases ASL depth in IL-13-treated cultures.
Figure 6B:
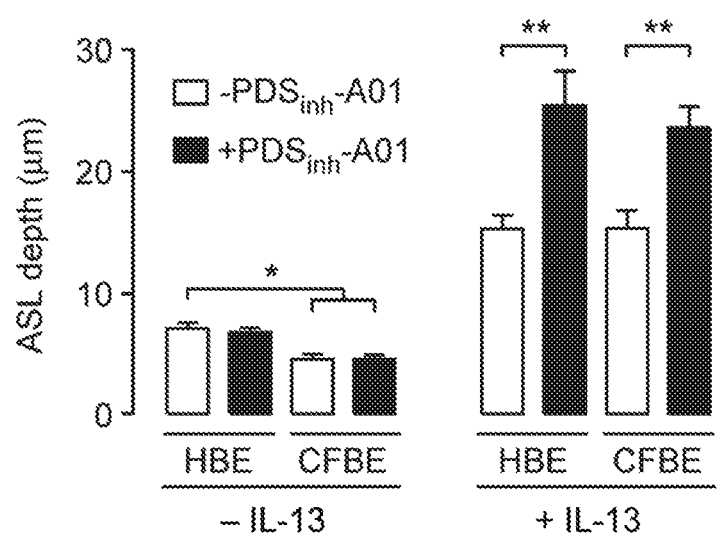

PDS$_{Inh}$-A01 Increases ASL Depth in IL-13-Treated Primary Human Bronchial Epithelial Cell Cultures ASL depth was measured in HBE and CFBE cell cultures under basal conditions and with chronic IL-13-treatment. CFBE cell cultures showed reduced ASL depth compared to HBE cell cultures in the absence of IL-13-treatment (~8 µm versus ~5 µm; FIG. 6A, left; summary in FIG. 6B), in agreement with prior studies. Under these basal conditions, treatment of HBE or CFBE cell cultures with 25 µM PDS$_{inh}$-A01 did not significantly change ASL depth. Treatment of HBE and CFBE cell cultures with IL-13 produced a significant increase in ASL depth to ~16 µm. Remarkably, treatment of IL-13-treated HBE and CFBE cell cultures with PDS$_{inh}$-A01 produced a significant further increase in ASL depth of ~8 µm (FIG. 6A, right; summary in FIG. 6B). Pendrin inhibition thus causes ASL hydration in IL-13-treated HBE and CFBE cell cultures, providing pharmacological evidence for pendrin as a key regulator of ASL hydration in airway cell cultures exposed to an inflammatory stimulant.

ASL depth was measured by confocal imaging of rhodamine B-dextran fluorescence (20 µl of 0.1 mg/ml in PBS) applied 4-6 h prior to measurement. Scanning confocal microscopy was done using an upright Nikon EZ-C1 confocal microscope equipped with a LUMplan FL N 60x/1.00w objective (Olympus, Waltham, Mass.). For measurements the transwell filter containing cells with fluorescently stained ASL was inverted, with the immersion objective contacting a droplet of PBS added onto the upper-facing basal surface of the transwell filter. In some experiments ASL depth was measured after treatment with 25 μM PDS$_{inh}$-A01 in the culture medium for 4-6 hours. ASL depth was measured using a multi-point histogram method in which each confocal z-stack was fitted to a quadratic function, as described and validated previously.

Without wishing to be bound by theory, it is believed that as pendrin mediates electroneutral Cl$^-$/HCO$_3^-$ exchange, pendrin activity will produce net osmol movement into the cell because some HCO$_3^-$ in the ASL becomes protonated and liberates CO$_2$; pendrin inhibition may therefore increase ASL volume in the steady-state.

In CF, defective Cl$^-$ and HCO$_3^-$ transport into the ASL alters salt and water transport, promoting ASL volume depletion. There is a considerable body of evidence linking ASL volume dysregulation in CF to impaired immune functions and CF disease pathogenesis. Rehydration of the airway surface is thus considered to be a useful therapeutic approach in CF. Evidence from confocal microscopy, transmission electron microscopy and fluorescence photobleaching indicate that the ASL consists of two discrete layers: a superficial mucus layer (ML) that contains large gel-forming mucins (MUC5AC and MUC5B) that trap particulates for subsequent mucociliary clearance, and in contact with cells and cilia, a periciliary layer (PCL) that contains large membrane-bound mucins (MUC1 and MUC4). Classically, the ASL was considered to consist of a mucus gel supported on a water-like liquid layer surrounding cilia ('gel-on-liquid' model). More recently, Button and colleagues showed that tethered mucins in the PCL form a mesh to prevent entry of gel-forming mucins and support ciliary beating, and proposed a 'gel-on-brush' model to describe the ASL. Photobleaching studies support this concept and have established that the fluid phase viscosity of the ML and PCL are similar in non-CF subjects (7-10-times more viscous than saline), but significantly elevated in both regions in CF cultures (25-30-times more viscous than saline). In addition to forming a permeability barrier, tethered mucins in the PCL generate an osmotic pressure to regulate PCL hydration. The osmotic potential exerted by CF mucus (>8% solids), but not healthy mucus (~2% solids), was demonstrated to be sufficient to dehydrate the PCL and collapse cilia, and to restrict mobility of bacteria and foster formation of bacterial biofilm precursor macrocolonies. Restoration of CFTR expression in CF primary epithelial cells by viral transduction significantly increases ASL depth, ciliary beat frequency and mucus transport, supporting the idea that loss of CFTR function mediates ASL dehydration. Therefore, the bulk of available evidence links reduced ASL volume to increased propensity for infection, with reduced CFTR ion transport leading to reduced mucin hydration in the ML followed by PCL dehydration, ciliary collapse, mucostasis and bacterial colonization.

Example 7

Further Characterization of the Pendrin Inhibitor PDS$_{INH}$-C01

PDS$_{INH}$-C01 was further examined for pendrin inhibition and diuretic activity. PDS$_{inh}$-C01 was purchased from ChemDiv (San Diego Calif., USA). Other chemicals were purchased from Sigma unless otherwise stated. A plasmid expressing murine pendrin was generated in pcDNA3.1 (Invitrogen). A plasmid encoding murine Slc12a3 (NCC) was purchased from Dharmacon, and plasmids encoding murine Slc4a1 (AE1) and myc-tagged murine Slc26a3 (CLD/DRA) were from Origene. A plasmid encoding human NKCC1 (94% sequence similarity to murine NKCC1) was provided by B. Forbush (Yale).

Figure 7A:
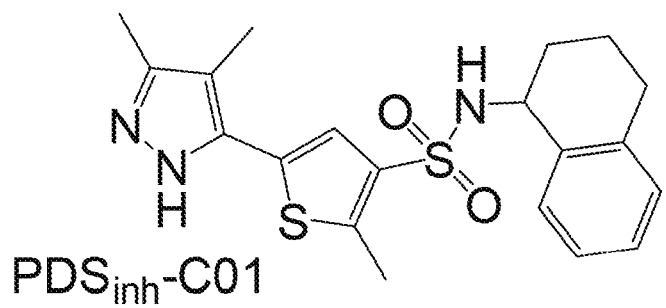
FIGS. 7A-7F further characterize a pendrin-inhibiting compound of the present disclosure and show representative data from pendrin-inhibition experiments in FRT cells.
Figure 7A:
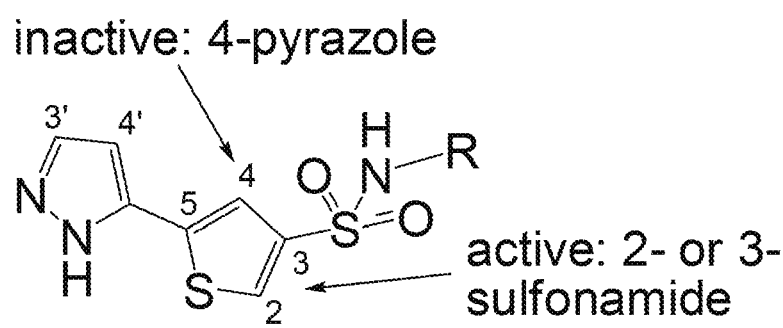
Figure 7A:
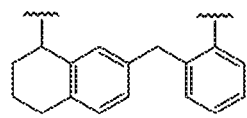
Figure 7A:
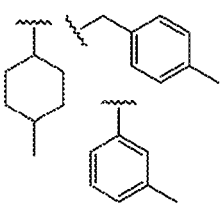
Figure 7A:
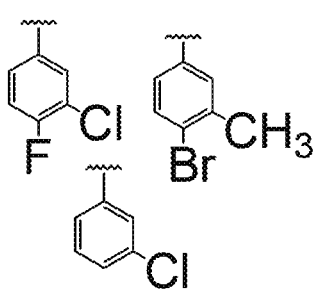
Figure 7B:
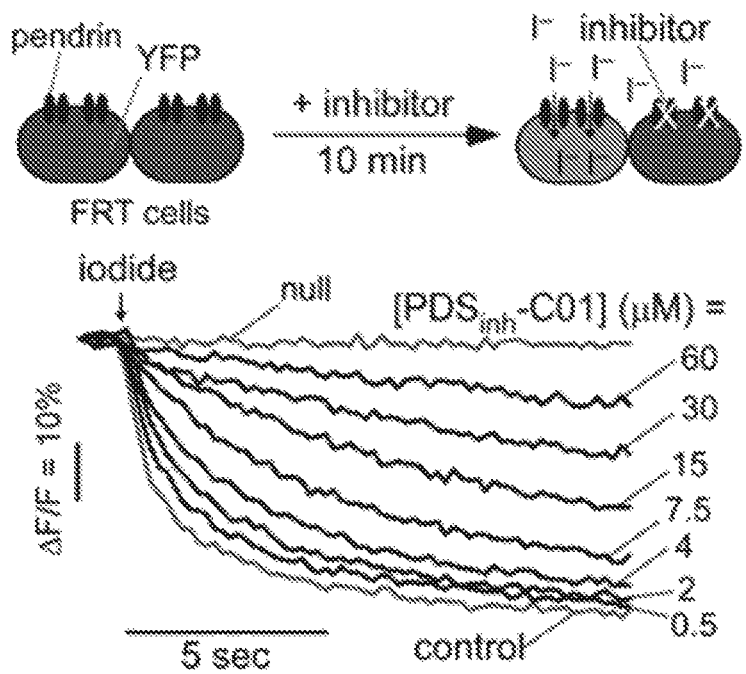

Functional studies of pendrin-mediated Cl$^-$ exchange for I$^-$, SCN$^-$ and NO$_3^-$ were done in FRT cells stably expressing murine pendrin and a YFP halide-sensing fluorescent indicator (FIG. 7B). Fischer rat thyroid (FRT) cells were cultured in Kaign's modified Ham's F12 medium supplemented with 10% FBS, 2 mM L-glutamine, 100 U/ml penicillin, 100 mg/ml streptomycin, 18 mg/ml myo-inositol and 45 mg/ml ascorbic acid. FRT cells stably expressing murine pendrin (from plasmid) and EYFP-H148Q/I152L/F46L (referred to as YFP) (by lentivirus) were generated by limiting dilution and selection using 0.5 mg/ml G418. COS-7 fibroblasts were cultured in DMEM-H21 supplemented with 10% FBS, 2 mM L-glutamine, 100 U/ml penicillin and 100 mg/ml streptomycin and transiently transfected with cDNAs encoding YFP and various membrane transporters using Lipofectamine 2000.

Pendrin-mediated exchange of Cl$^-$ with SCN$^-$, I$^-$ or NO$_3^-$ was measured from the kinetics of YFP fluorescence quenching in a BMG FLUOstar Omega platereader. Pendrin/YFP-expressing FRT cells were washed in PBS and transport measured following a 70-mM gradient of SCN$^-$, I$^-$ or NO$_3^-$. Pendrin-mediated Cl$^-$/HCO$_3^-$ exchange was measured from the kinetics of cytoplasmic pH (pHi) using BCECF-AM (Invitrogen). Pendrin-expressing FRT cells in HCO$_3^-$-containing buffer (in mM: 120 NaCl, 5 KCl, 1 CaCl$_2$), 1 MgSO$_4$, 10 glucose, 5 Hepes, 25 NaHCO$_3^-$; pH 7.4; 95% O$_2$/5% CO$_2$ equilibrated) were exposed to a Cl$^-$-free buffer (gluconate replacing Cl$^-$) to drive Cl$^-$ efflux and HCO$_3^-$ influx.

Figure 7C:
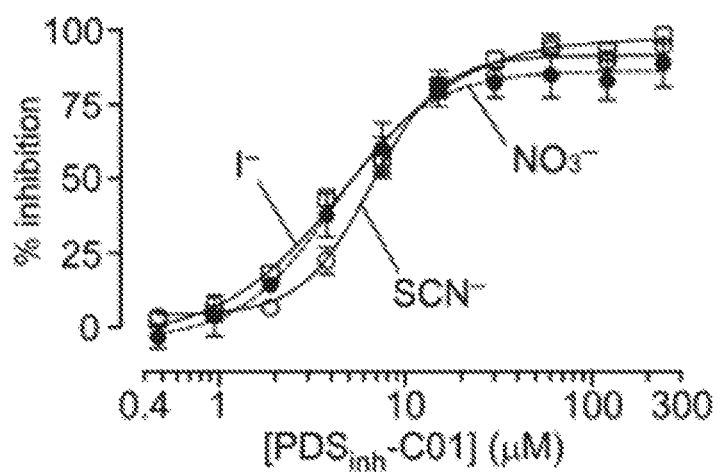
Figure 7D:
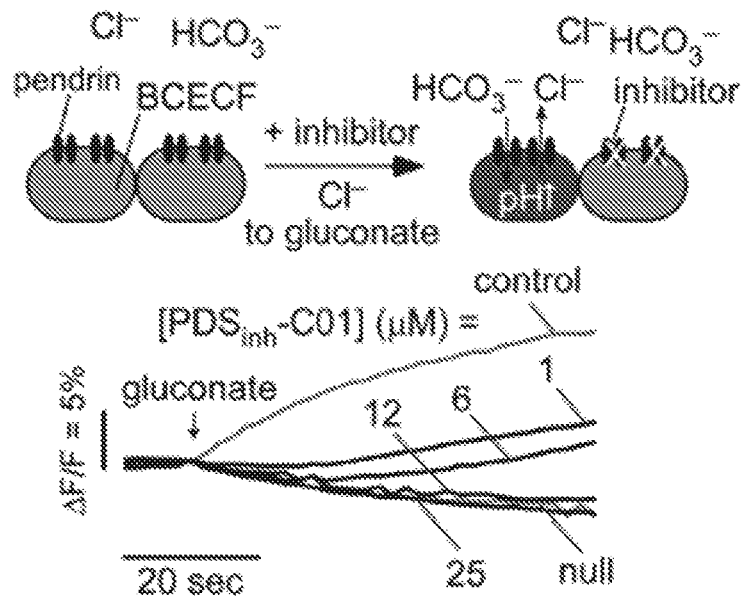
Figure 7E:
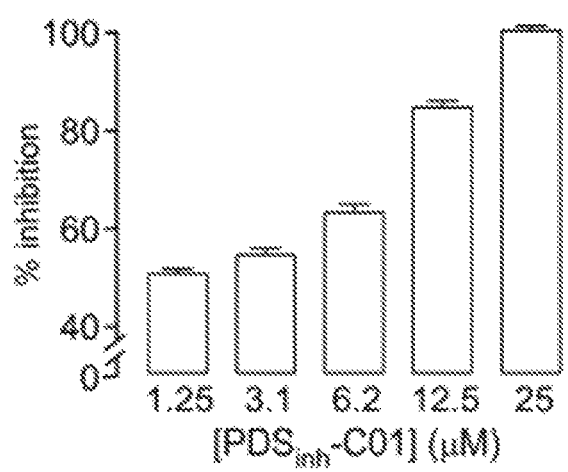
Figure 7F:
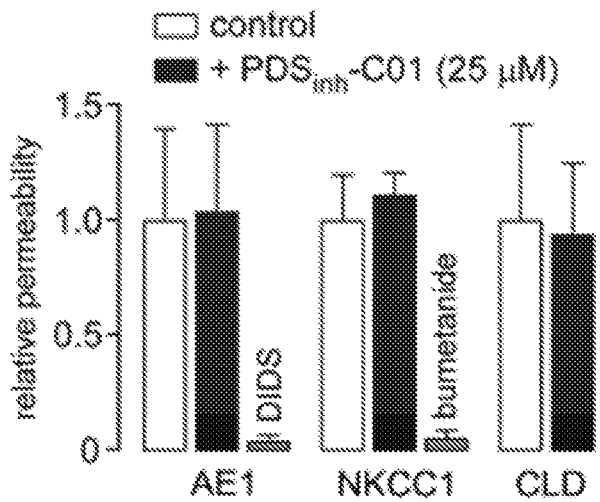

As shown in FIG. 7B, addition of I$^-$ to the extracellular solution caused YFP fluorescence quenching in pendrin expressing cells, with near-zero quenching in cells expressing YFP alone. Pendrin inhibition by PDS$_{inh}$-C01 reduced the rate of fluorescence quenching (as a function of Cl$^-$ exchange with I$^-$, SCN$^-$ or NO$_3^-$) in a concentration-dependent manner (FIG. 7C). Pendrin-mediated Cl$^-$/HCO$_3^-$ exchange was measured from the kinetics of intracellular pH, using BCECF fluorescence as a cytoplasmic pH sensor, following extracellular addition of gluconate in HCO$_3^-$/CO$_2$-containing buffer to drive Cl-efflux, HCO$_3^-$ influx, and consequent cytoplasmic alkalinization (FIG. 7D). PDS$_{inh}$-C01 reduced the kinetics of Cl$^-$/HCO$_3^-$ exchange, the activity of pendrin of relevance to kidney function, in a concentration-dependent manner with IC$_{50}$~1.2 μM (FIG. 7E). In selectivity studies, PDS$_{inh}$-C01 at 25 μM did not significantly inhibit the transport activities of Slc4a1 (AE1), Slc26a3 (CLD/DRA) or NKCC1 (Slc12a2) (FIG. 7F). YFP-based fluorescence quenching assays in COS-7 cells were established to measure AE1 (Slc4a1), CLD (Slc26a3) and NCC (Slc12a3) activities. For AE1 assay, cells expressing YFP and AE1 were equilibrated in PBS and then subjected to a 70-mM SCN$^-$ gradient (SCN$^-$ replacing Cl$^-$). For CLD assay, cells expressing YFP and CLD were subjected to a 102-mM SCN$^-$ gradient. For NCC activity, cells expressing YFP and NCC were equilibrated for 1 h in Na gluconate-substituted PBS and then subjected to a 70-mM I$^-$ gradient. A YFP-V163S fluorescence quenching assay in FRT cells was used to measure NKCC1 activity in which cells equilibrated gluconate-substituted PBS buffer were exposed to a Cl$^-$-containing solution containing 75 mM Na$^+$ and 75 mM K$^+$.

Example 8

Pharmacokinetics of PDS$_{Inh}$-C01 in Mice

Pharmacokinetics measurements were done to guide studies of diuretic efficacy. Animal experiments were approved by UCSF Institutional Animal Care and Use Committee. Female CD1 mice (8-10 weeks) were injected with 10 mg/kg PDS$_{inh}$-C01 (in saline containing 5% DMSO and 10% Kolliphor HS) ip and blood was collected by orbital puncture at 15, 30, 60, 150 and 240 min, and centrifuged at 5000 rpm for 15 min to separate plasma. Urine was collected in metabolic cages. An LC/MS method was developed to measure PDS$_{inh}$-C01 concentrations in mouse blood and urine. Plasma and urine samples (60 μL) were mixed with 300-μL acetonitrile and centrifuged at 13000 rpm for 20 min, and 90 μL of the supernatant was taken for liquid chromatography/mass spectrometry (LC/MS; Waters 2695 and Micromass ZQ). The solvent system consisted of a linear gradient from 5 to 95% acetonitrile over 16 min. Sodium and potassium concentrations in 3-h collected urine samples were measured by flame photometry (PFP7 Clinical Flame Photometer, Bibby Scientific Ltd, Stone. Staffs, UK). For blood gas analysis, arterial blood was collected from the abdominal aorta under isoflurane anesthesia 3 h after treatment. Blood gas was analyzed by iSTAT1 with CG4+ cartridges (Abbott Laboratories, Abbott Park, IL, USA). Urine pH was measured on freshly collected urine samples using an AB 15 pH Meter (Fisher Scientific, Pittsburgh, Pa., USA). Experiments with two groups were analyzed with Student's t-test, and experiments with 3 or more groups were analyzed using one-way analysis of variance and post-hoc Newman-Keuls multiple comparisons test. $P<0.05$ was taken as statistically significant.

Figure 8A:
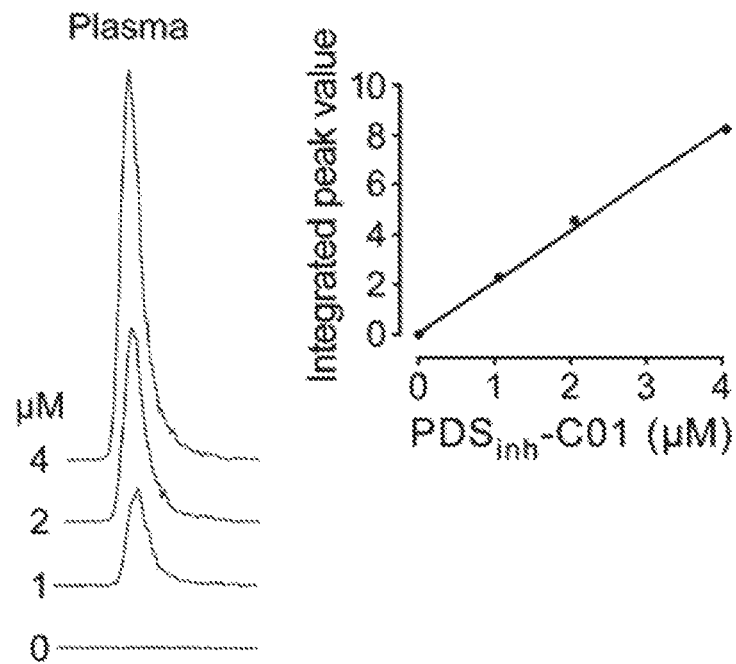
FIGS. 8A-8D present $PDS_{inh}$-C01 pharmacokinetics data in mouse urine and plasma. These data were used to guide studies of diuretic efficacy.
Figure 8B:
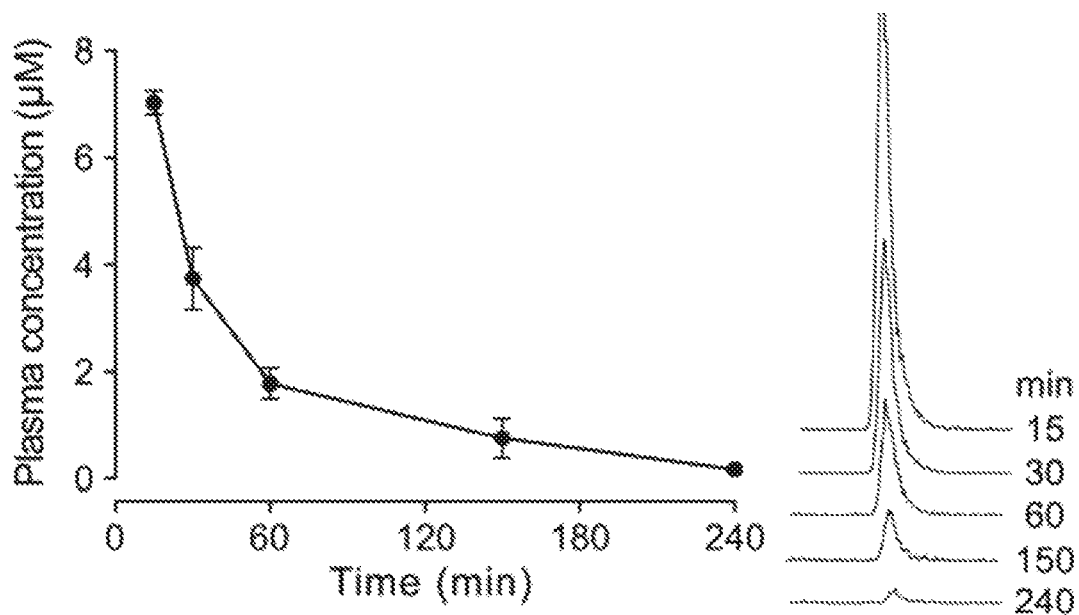
Figure 8C:
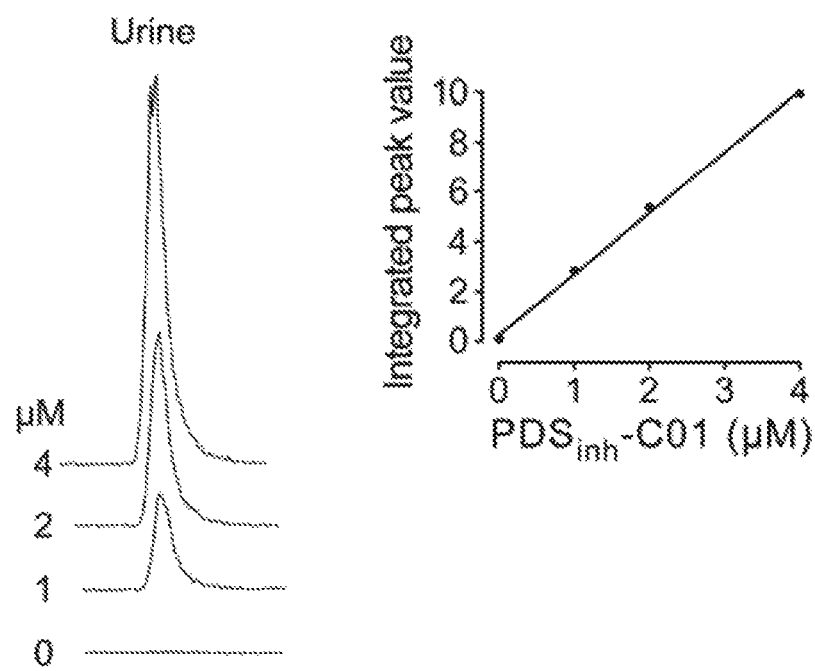
Figure 8D:
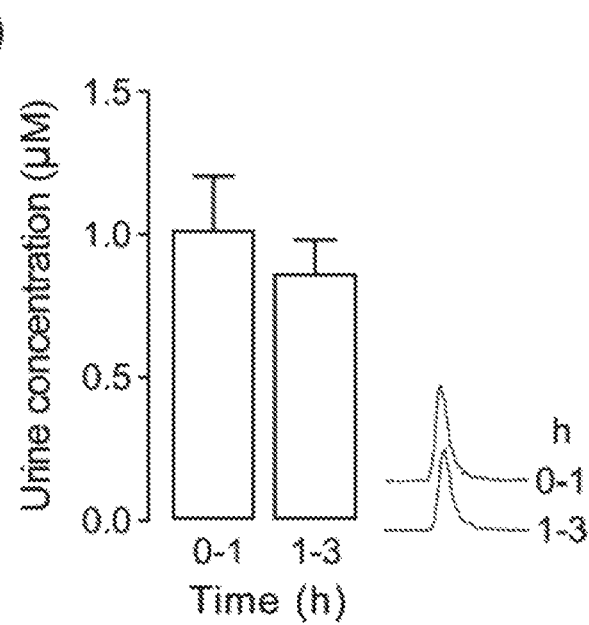

FIGS. 8A and 8C show original LC/MS data and linear standard curves in plasma and urine in which known amounts of PDS$_{inh}$-C01 were added to plasma and urine from untreated mice. FIGS. 8B and 8D summarize PDS$_{inh}$-C01 concentrations in plasma and urine following bolus intraperitoneal (ip) administration of 10 mg/kg PDS$_{inh}$-C01, showing predicted therapeutic concentrations for several hours.

Example 9

Pendrin Inhibition Alone does not Affect Renal Function

Figure 9A:
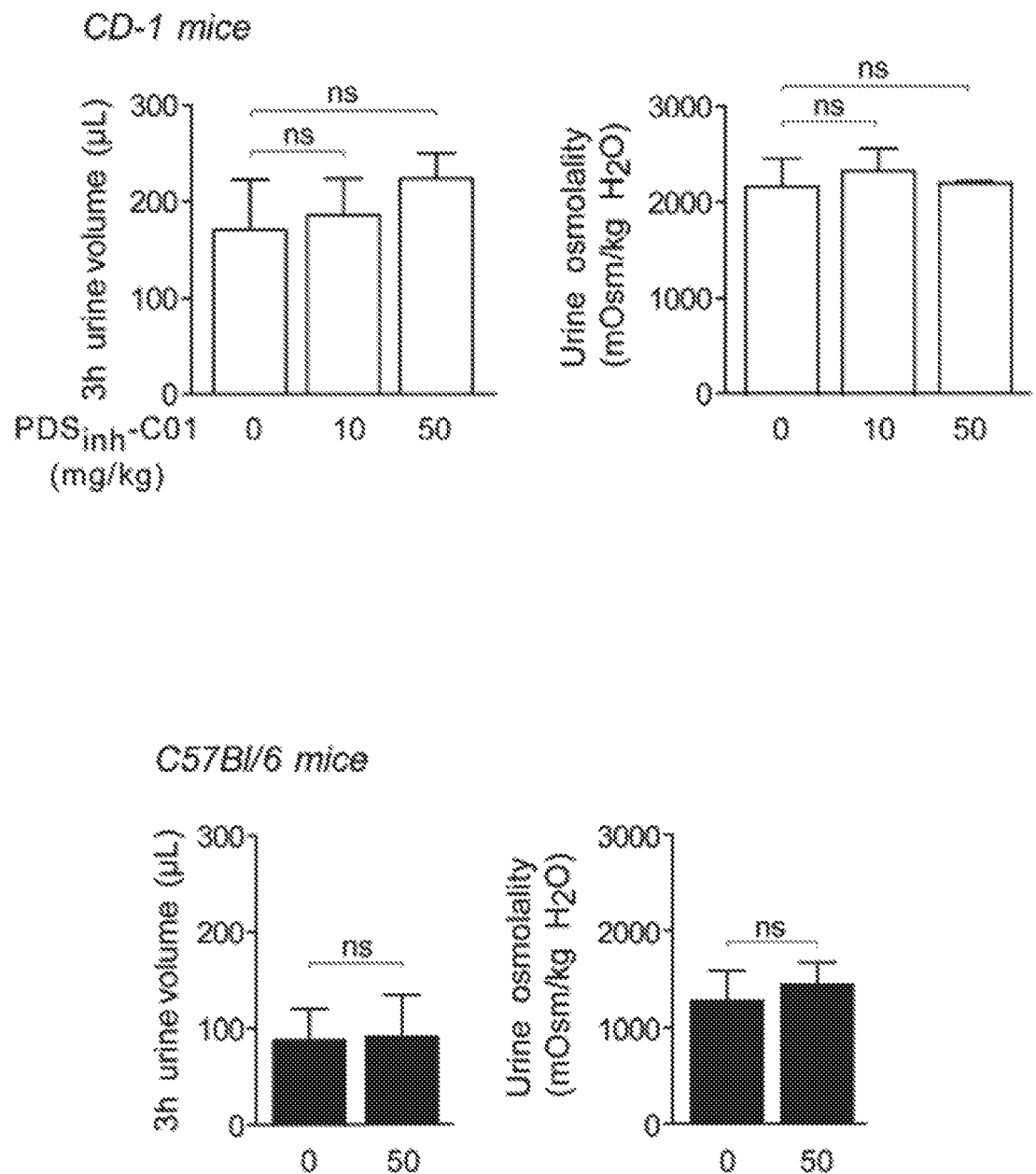
FIGS. 9A-9D illustrate that pendrin inhibition alone by $PDS_{inh}$-C01 does not affect renal function. $PDS_{inh}$-C01 was administered to mice by ip injection as done in the pharmacokinetics measurements.
Figure 9B:
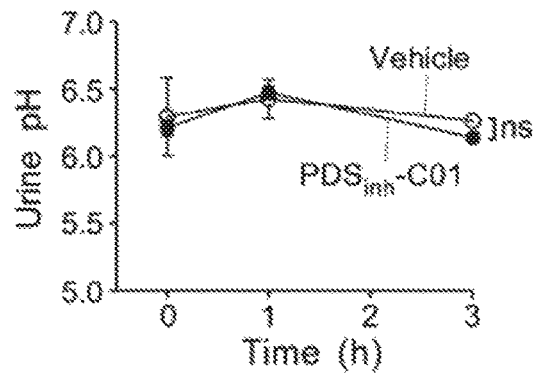
Figure 9C:
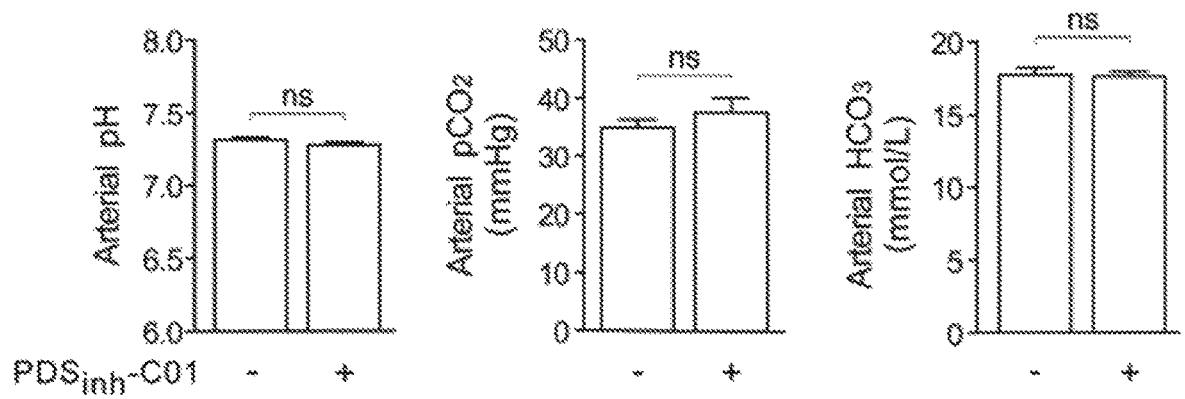
Figure 9D:
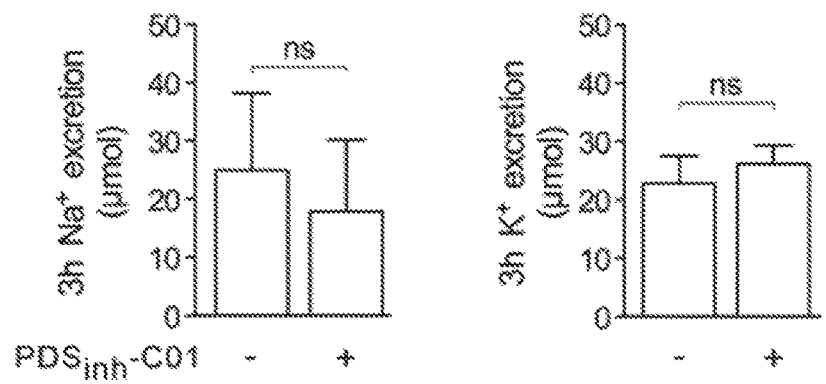

PDS$_{inh}$-C01 was administered to mice by ip injection as done in the pharmacokinetics measurements. FIG. 9A shows similar 3-h urine volume and osmolality in two different strains of mice (CD-1 and C57B/6) treated with vehicle or PDS$_{inh}$-C01. Even at a very high dose of 50 mg/kg, PDS$_{inh}$-C01 administration did not significantly change urine pH (FIG. 9B) or blood gas values (FIG. 9C), nor did it affect 3-h urinary salt excretion (FIG. 9D). Similar results were obtained using PDS$_{inh}$-A01 (data not shown).

Example 10

Pendrin Inhibition Potentiates the Acute Diuretic Action of Furosemide

Although pendrin inhibitors alone did not produce a diuretic response in mice, pendrin inhibition was shown to augment the diuretic response to acute administration of furosemide, a loop-diuretic that increases salt delivery to the pendrin-expressing CNT and CCD.

In acute studies, mice (both CD-1 and C57Bl/6 strains) were injected ip with 10 or 50 mg/kg PDS$_{inh}$-C01. In some experiments mice were treated with 10 mg/kg PDS$_{inh}$-C01 together with furosemide (5, 10, 20 or 50 mg/kg, ip). The mice were placed in individual metabolic cages and spontaneously voided urine was collected for 3 h for measurement of volume and osmolality (freezing point depression osmometry, Micro-osmometer; Precision Systems, Natick, Mass., USA).

Figure 10A:
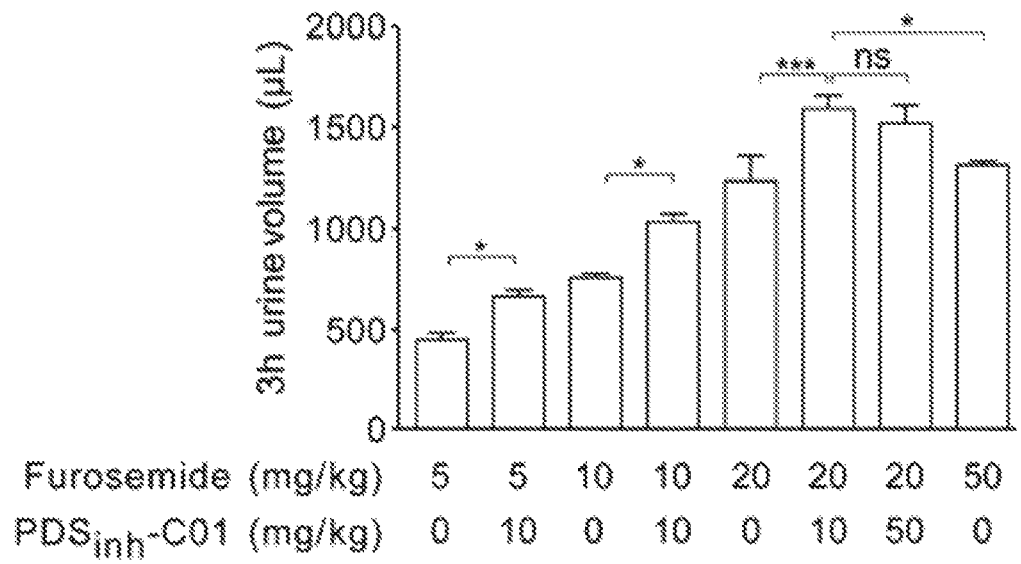
FIGS. 10A-10E illustrate that pendrin inhibition potentiates the diuretic action of furosemide in an acute treatment model.
Figure 10A:
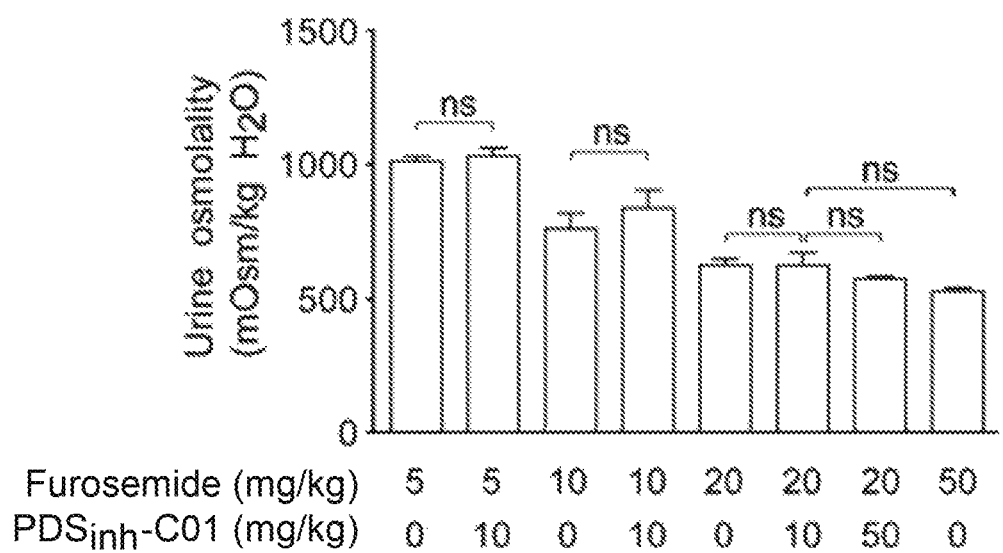
Figure 10B:
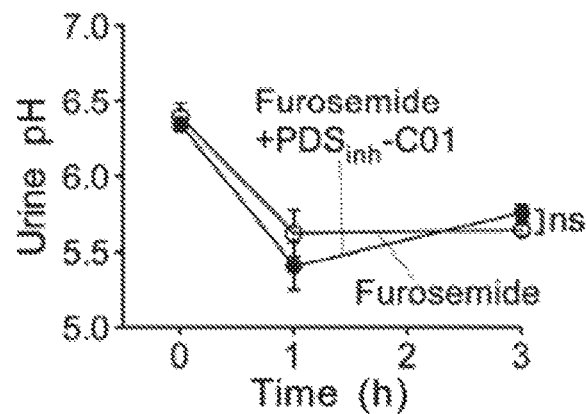
Figure 10C:
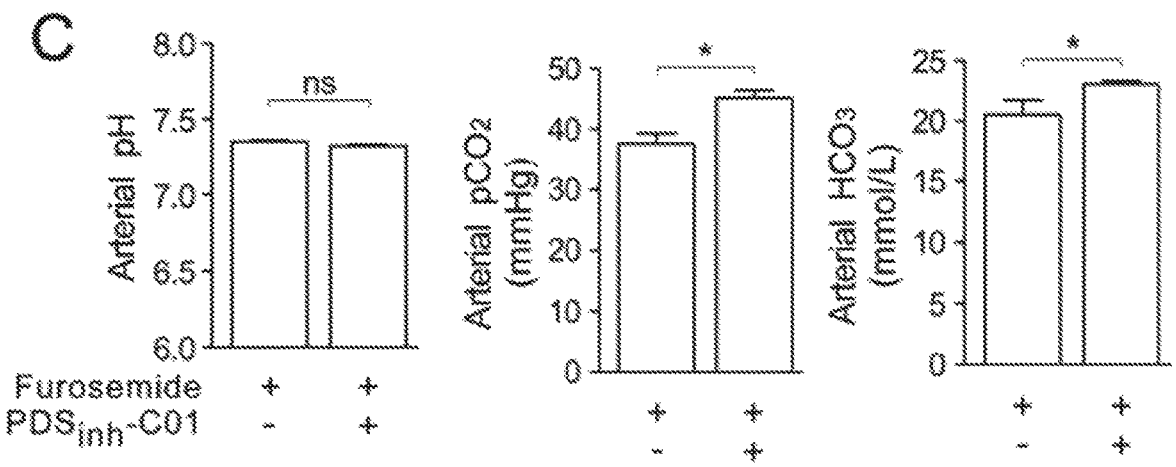
Figure 10D:
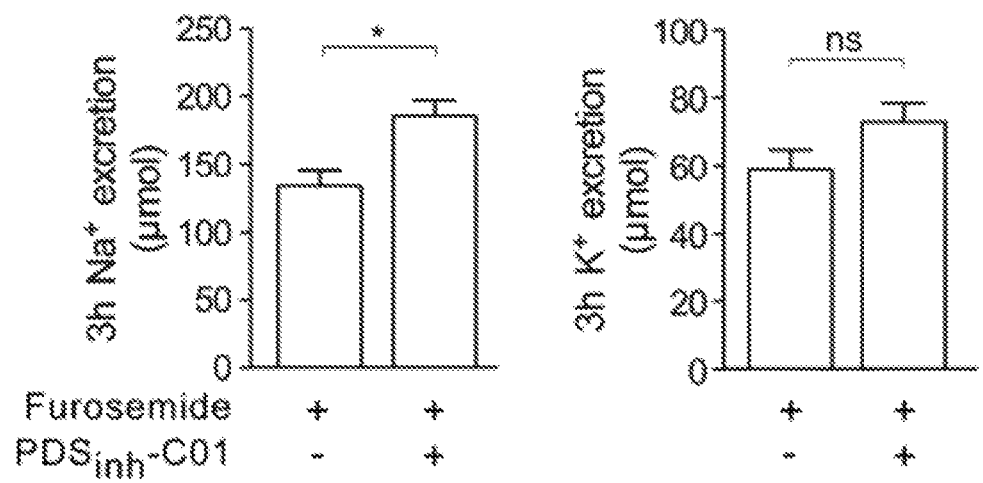
Figure 10E:
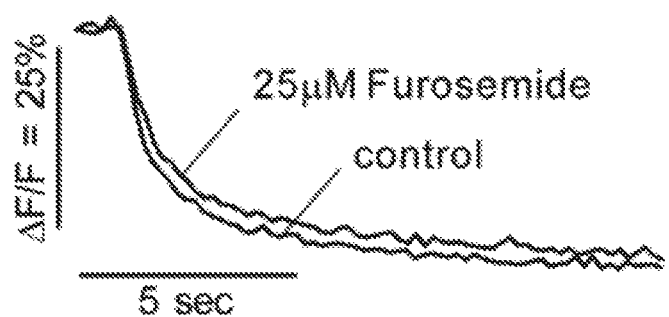

Mice were administered furosemide and PDS$_{inh}$-C01 (or vehicle) ip at zero time, and urine was collected for the next 3 hours. FIG. 10A shows that PDS$_{inh}$-C01 (10 mg/kg) significantly increased urine volume by ~30% at each dose of furosemide tested, without effect on urine osmolality. The diuretic effect was significantly greater than that produced by maximal furosemide (50 mg/kg). Increasing PDS$_{inh}$-C01 dose to 50 mg/kg did not further potentiate the furosemide effect. PDS$_{inh}$-C01, when given with 20 mg/kg furosemide, did not affect urine pH (FIG. 10B), but produced a compensated metabolic alkalosis (FIG. 10C). PDS$_{inh}$-C01 increased 3-h urinary Na+ excretion, with no significant effect on K+ excretion (FIG. 10D). Similar results were obtained using PDS$_{inh}$-C01 (data not shown). To rule out an inhibitory effect of furosemide on pendrin activity that could confound the physiological data, in vitro measurements showed no effect of furosemide on pendrin activity (FIG. 10E).

Example 11

Pendrin Inhibition Potentiates the Chronical Diuretic Action of Furosemide

Because chronic loop diuretic treatment upregulates renal pendrin expression, which might potentiate the diuretic efficacy of pendrin inhibition, the action of PDS$_{inh}$-C01 in a chronic furosemide treatment model.

Figure 11A:
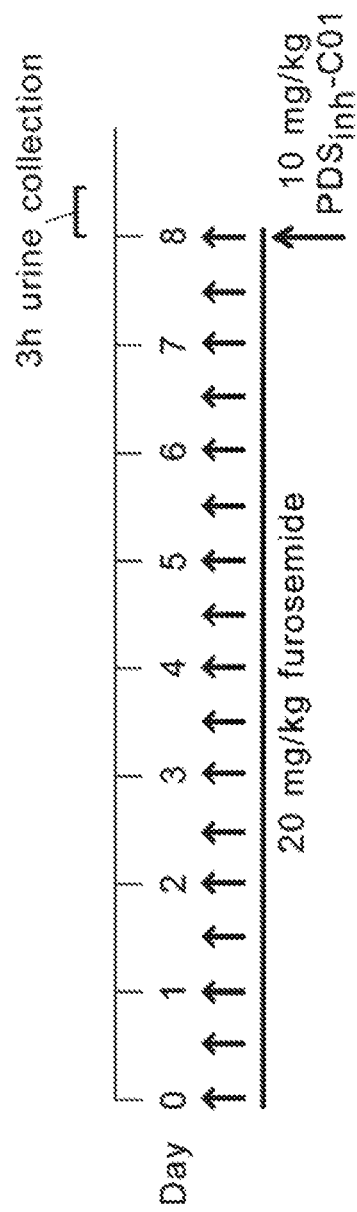

In chronic studies, mice were injected with 20 mg/kg furosemide (ip) twice a day for 8 days and then administered PDSinh-C01 (10 mg/kg) or vehicle at the time of the final furosemide dose. See FIG. 11A. Urine was collected for 3 h as described above.

After 8 days of furosemide treatment, PDS$_{inh}$-C01 further potentiated the furosemide effect. FIG. 11B shows a ~60% increase in urine volume following PDS$_{inh}$-C01 in the chronically furosemide-treated mice, without effect on urine osmolality. PDS$_{inh}$-C01 significantly increased urinary Na$^+$ and K$^+$ excretion (FIG. 11C). Similar results were obtained using PDS$_{inh}$-A01 (data not shown).

The various embodiments described above can be combined to provide further embodiments. All U.S. patents, U.S. patent application publications, U.S. patent applications, foreign patents, foreign patent applications, and non-patent publications referred to in this specification and/or listed in the Application Data Sheet are incorporated herein by reference, in their entirety. Aspects of the embodiments can be modified, if necessary to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:
1. A pharmaceutical composition comprising a pharmaceutically acceptable excipient and a compound represented by Formula (Ia):

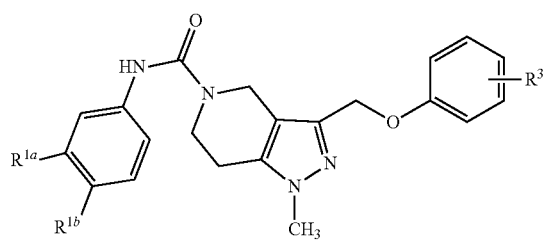

(Ia)

wherein,
- $R^{1a}$ and $R^{1b}$ are the same or different and independently hydrogen, optionally substituted alkyl, optionally substituted alkoxy, halo, trifluoroalkyl, or optionally substituted thioalkyl;
- $R^3$ is hydrogen or halo, provided that when $R^{1b}$ is alkyl, $R^3$ is halo,
- wherein optionally substituted may be unsubstituted or substituted in which at least one hydrogen atom is replaced with a substituent selected from the group consisting of oxo, $CO_2H$, nitrile, nitro, $CONH_2$, hydroxyl, thiooxy, alkyl, alkylene, alkoxy, alkoxyalkyl, alkylcarbonyl, alkyloxycarbonyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cycloalkyloxycarbonyl, heterocyclyl, heteroaryl, dialkylamines, arylamines, alkylarylamines, diarylamines, N-oxides, imide, enamine, trialkylsilyl, dialkylarylsilyl, alkyldiarylsilyl, thioalkyl triarylsilyl, perfluoroalkyl, perfluoroalkoxy, $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SO_2R_g$, $-OSO_2R_g$, $-SO_2OR_g$, $=NSO_2R_g$, $-SO_2NR_gR_h$, $-C(=O)R_g$, $-C(=O)OR_g$, $-CH_2SO_2R_g$, $-CH_2SO_2NR_gR_h$, $-SH$, $-SR_g$ and $-SSR_g$, wherein $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl.

2. The pharmaceutical composition of claim 1 wherein $R^{1a}$ and $R^{1b}$ are the same or different and independently methyl, ethyl, methoxy, thiomethyl, trifluoromethyl, fluoro, or chloro.

3. The pharmaceutical composition of claim 1 comprising at last one compound selected from the group consisting of:

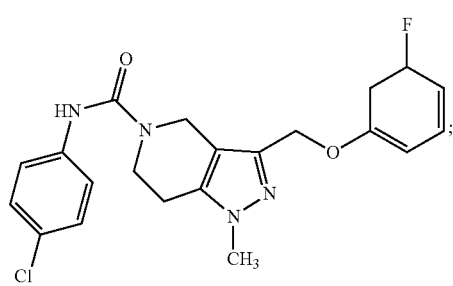

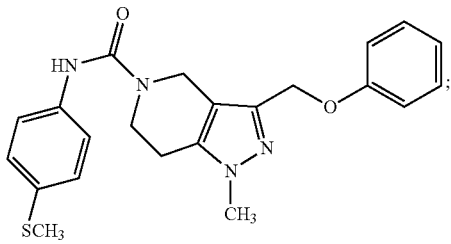

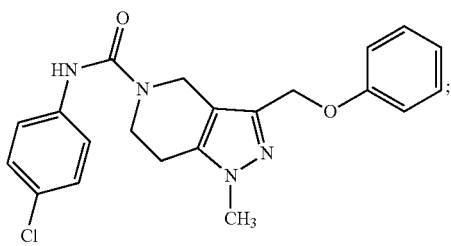

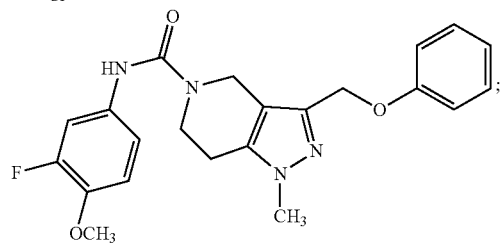

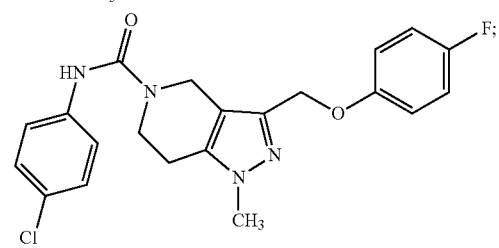

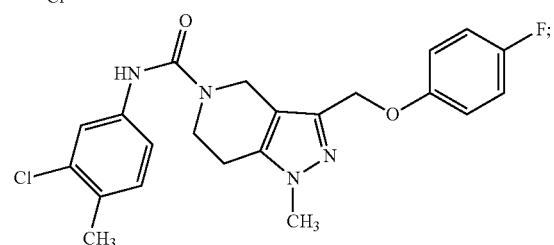

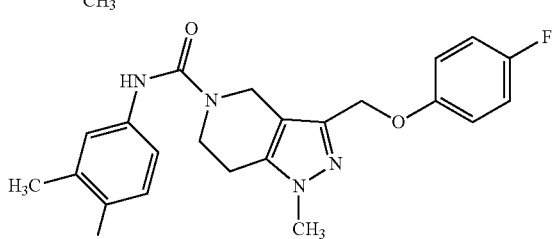

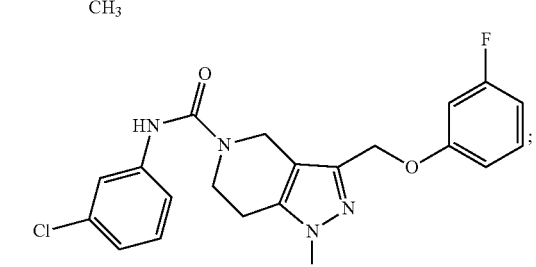

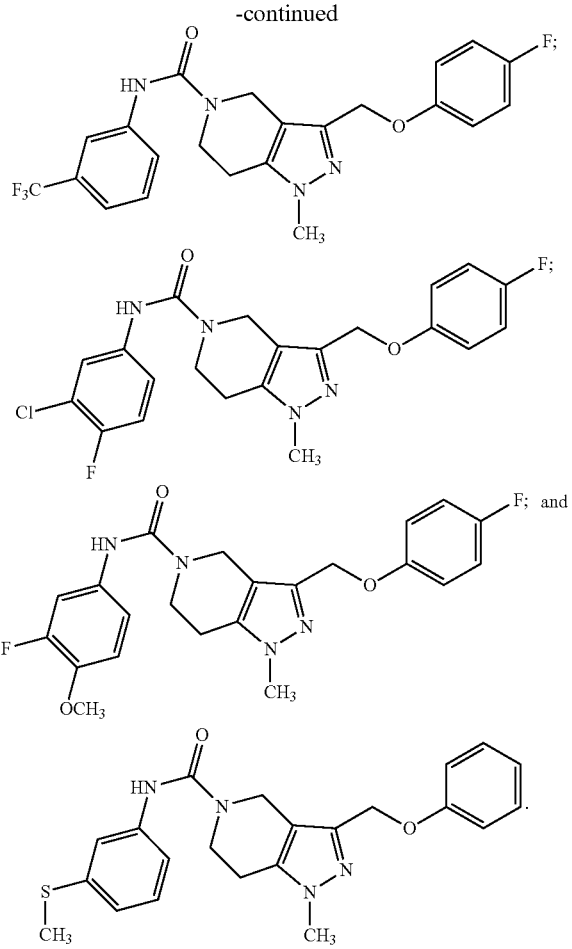

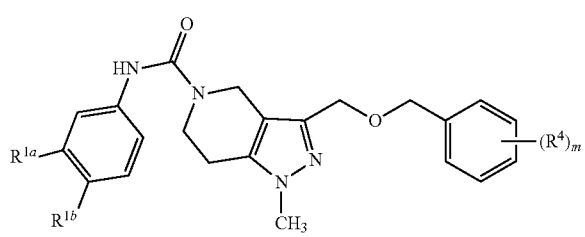

4. A pharmaceutical composition comprising a pharmaceutically acceptable excipient and a compound represented by Formula (Ib):

(Ib)

wherein,
m is 0, 1 or 2;
$R^{1a}$ and $R^{1b}$ are the same or different and independently hydrogen, optionally substituted alkyl, optionally substituted alkoxy, halo, trifluoroalkyl, or optionally substituted thioalkyl; and
each $R^4$ is the same or different and independently halo, wherein optionally substituted may be unsubstituted or substituted in which at least one hydrogen atom is replaced with a substituent selected from the group consisting of oxo, $CO_2H$, nitrile, nitro, $CONH_2$, hydroxyl, thiooxy, alkyl, alkylene, alkoxy, alkoxyalkyl, alkylcarbonyl, alkyloxycarbonyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cycloalkyloxycarbonyl, heterocyclyl, heteroaryl, dialkylamines, arylamines, alkylarylamines, diarylamines, N-oxides, imide, enamine, trialkylsilyl, dialkylarylsilyl, alkyldiarylsilyl, thioalkyl triarylsilyl, perfluoroalkyl, perfluoroalkoxy, $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SO_2R_g$, $-OSO_2R_g$, $-SO_2OR_g$, $=NSO_2R_g$, $-SO_2NR_gR_h$, $-C(=O)R$, $-C(=O)OR_g$, $-CH_2SO_2R_g$, $-CH_2SO_2NR_gR_h$, $-SH$, $-SR_g$ and $-SSR_g$, wherein $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl.

5. The pharmaceutical composition of claim 4 wherein $R^{1a}$ and $R^{1b}$ are the same or different and independently methyl, ethyl, methoxy, thiomethyl, fluoro or chloro.

6. The pharmaceutical composition of claim 4 comprising at last one compound selected from the group consisting of:

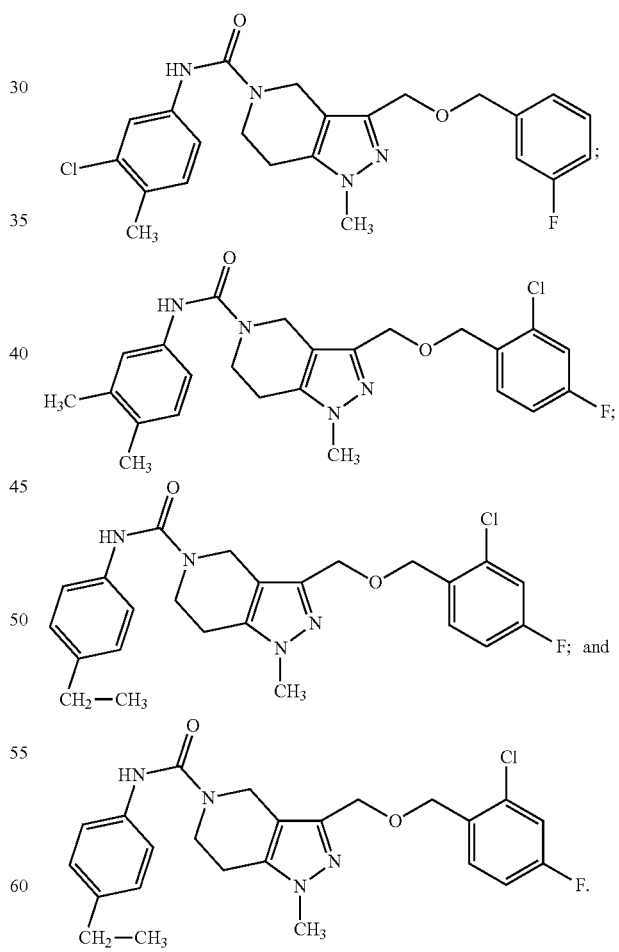

7. A pharmaceutical composition comprising a pharmaceutically acceptable excipient and a pyrazolothiophenesulfonamide compound represented by Formula (II):

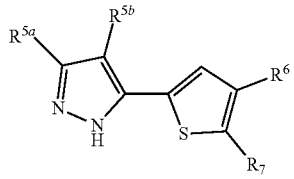

(II)

wherein, $R^{5a}$ and $R^{5b}$ are the same or different and independently hydrogen, or optionally substituted alkyl, provided that $R^{5a}$ and $R^{5b}$ are not both hydrogen;

$R^6$ and $R^7$ are the same or different and independently hydrogen, optionally substituted alkyl, or —S(O)$_2$NHR, provided one of $R^6$ and $R^7$ is —S(O)$_2$NHR; and R is optionally substituted aryl or optionally substituted cycloalkyl, wherein optionally substituted may be unsubstituted or substituted in which at least one hydrogen atom is replaced with a substituent selected from the group consisting of oxo, CO$_2$H, nitrile, nitro, CONH$_2$, hydroxyl, thiooxy, alkyl, alkylene, alkoxy, alkoxyalkyl, alkylcarbonyl, alkyloxycarbonyl, aryl, aralkyl, arylcarbonyl, aryloxycarbonyl, aralkylcarbonyl, aralkyloxycarbonyl, aryloxy, cycloalkyl, cycloalkylalkyl, cycloalkylcarbonyl, cycloalkylalkylcarbonyl, cycloalkyloxycarbonyl, heterocyclyl, heteroaryl, dialkylamines, arylamines, alkylarylamines, diarylamines, N-oxides, imide, enamine, trialkylsilyl, dialkylarylsilyl, alkyldiarylsilyl, thioalkyl triarylsilyl, perfluoroalkyl, perfluoroalkoxy, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, —SO$_2$NR$_g$R$_h$, —C(=O)R$_g$, —C(=O)OR$_g$, —CH$_2$SO$_2$R$_g$, —CH$_2$SO$_2$NR$_g$R$_h$, —SH, —SR$_g$ and —SSR$_g$, wherein R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl.

8. The pharmaceutical composition of claim 7 wherein R is tetrahydronaphthalenyl, phenyl optionally substituted by alkyl, cyclohexyl, cyclopentyl or a combination thereof.

9. The pharmaceutical composition of claim 7 comprising at last one compound selected from the group consisting of:

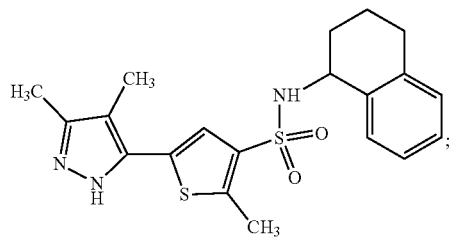

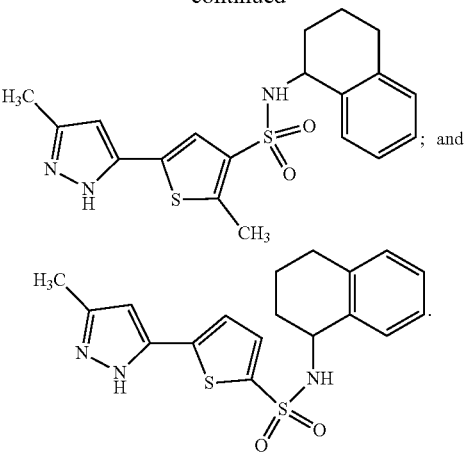

10. A method of treating an airway disease in a subject in need thereof comprising administering to the subject a therapeutically effective amount of the pharmaceutical composition of claim 1, wherein the airway diseases is an inflammatory lung disease, cystic fibrosis, rhinovirus infection, rhinitis, chronic rhinosinusitis, sinusitis, or airway diseases caused by viral or bacterial infections, or by exposure to industrial toxins.

11. A method for treating a disease or condition treatable by inhibiting pendrin, partially or completely, in a subject, the method comprising administering a pharmaceutical composition comprising a pharmaceutically acceptable excipient and the pharmaceutical composition of claim 1, wherein the disease or condition treatable by inhibiting pendrin is cystic fibrosis, asthma, chronic obstructive pulmonary disease, rhinitis, sinusitis, hypertension, edema, or aberrant thyroid activity.

12. A method of promoting diuresis to a subject in need thereof comprising:
administering to the subject a diuretic; and
administering to the subject a therapeutically effective amount of the pharmaceutical composition of claim 1, wherein the pharmaceutical composition is administered prior to, contemporaneous with, or following administration of the diuretic to the subject.

13. The method of claim 12 wherein the diuretic is a thiazide compound selected from the group consisting of furosemide, azosemide, bumelanide, piretanide, and torasemide.

14. A method for treating hypertension or edema in a subject in need thereof comprising:
administering to the subject a diuretic; and
administering to the subject a therapeutically effective amount of the pharmaceutical composition of claim 1, wherein the pharmaceutical composition is administered prior to, contemporaneous with, or following administration of the diuretic to the subject.

15. A method of treating hypertension comprising administering to a subject in need thereof a therapeutically effective amount of the pharmaceutical composition claim 1.

16. A method of treating a thyroid condition comprising administering to a subject in need thereof a therapeutically effective amount of the pharmaceutical composition claim 1.

17. A method of treating an airway disease in a subject in need thereof comprising administering to the subject a therapeutically effective amount of the pharmaceutical composition of claim 4, wherein the airway diseases is an inflammatory lung disease, cystic fibrosis, rhinovirus infection, rhinitis, chronic rhinosinusitis, sinusitis, or airway diseases caused by viral or bacterial infections, or by exposure to industrial toxins.

18. A method of promoting diuresis, or treating hypertension or edema in a subject in need thereof, the method comprising:
   administering to the subject a diuretic; and
   administering to the subject a therapeutically effective amount of the pharmaceutical composition of claim 4, wherein the pharmaceutical composition is administered prior to, contemporaneous with, or following administration of the diuretic to the subject.

19. A method of treating a thyroid condition comprising administering to a subject in need thereof a therapeutically effective amount of the pharmaceutical composition claim 4.

\* \* \* \* \*

UNITED STATES PATENT AND TRADEMARK OFFICE
CERTIFICATE OF CORRECTION

PATENT NO. : 10,702,506 B2
APPLICATION NO. : 16/079019
DATED : July 7, 2020
INVENTOR(S) : Alan S. Verkman et al.

It is certified that error appears in the above-identified patent and that said Letters Patent is hereby corrected as shown below:

In the Specification

Column 1, Line 9:
Delete "EY013574".

In the Claims

Column 34, Claim 4, Line 11:
"-C(=O)R," should read: -- -C(=O)$R_g$,--.

Column 36, Claim 15, Line 60:
"composition claim 1." should read: --composition of claim 1.--.

Column 36, Claim 16, Line 63:
"composition claim 1." should read: --composition of claim 1.--.

Column 37, Claim 19, Line 16:
"composition claim 4." should read: --composition of claim 4.--.

Signed and Sealed this
Third Day of December, 2024

Katherine Kelly Vidal
*Director of the United States Patent and Trademark Office*